United States Patent
Wang et al.

(10) Patent No.: US 10,183,971 B2
(45) Date of Patent: Jan. 22, 2019

(54) SAA-DOMAIN-SPECIFIC ANTIBODIES AND PEPTIDE ANTAGONISTS AND USE THEREOF TO TREAT INFLAMMATORY DISEASES

(71) Applicant: The Feinstein Institute For Medical Research, Manhasset, NY (US)

(72) Inventors: Haichao Wang, Edison, NJ (US); Andrew E. Sama, Manhasset, NY (US); Wei Li, Plainview, NY (US); Kevin J. Tracey, Old Greenwich, CT (US)

(73) Assignee: The Feinstein Institute For Medical Research, Manhasset, NY (US)

( * ) Notice: Subject to any disclaimer, the term of this patent is extended or adjusted under 35 U.S.C. 154(b) by 0 days.

(21) Appl. No.: 15/259,269

(22) Filed: Sep. 8, 2016

(65) Prior Publication Data
US 2017/0029463 A1    Feb. 2, 2017

Related U.S. Application Data

(62) Division of application No. 14/326,710, filed on Jul. 9, 2014, now Pat. No. 9,458,232.

(60) Provisional application No. 61/846,749, filed on Jul. 16, 2013.

(51) Int. Cl.
| | | |
|---|---|---|
| *C07K 7/06* | (2006.01) | |
| *C07K 16/18* | (2006.01) | |
| *C07K 14/47* | (2006.01) | |
| *A61K 39/00* | (2006.01) | |

(52) U.S. Cl.
CPC ............ *C07K 7/06* (2013.01); *C07K 14/4711* (2013.01); *C07K 16/18* (2013.01); *A61K 2039/505* (2013.01); *C07K 2317/33* (2013.01); *C07K 2317/34* (2013.01); *C07K 2317/76* (2013.01); *C07K 2319/30* (2013.01)

(58) Field of Classification Search
None
See application file for complete search history.

(56) References Cited

U.S. PATENT DOCUMENTS 7,067,110 B1 *  6/2006  Gillies ............... A61K 39/0011
                                                         424/1.49

FOREIGN PATENT DOCUMENTS

| WO | 2001/21188 A1 | 3/2001 | |
|---|---|---|---|
| WO | 2004/111084 A2 | 12/2004 | |
| WO | WO2005/039588 | * 5/2005 | ........... A61K 31/519 |

OTHER PUBLICATIONS

Benkirane et al. Journal of Biolgical Chemisry, 1993; 268: 26279-26285 (Year: 1993).*
Yamada T et al., entitled "Generation and Characterization of Rat Monoclonal Antibodies Against Human Serum Amyloid A," Scand. J. Immunol. 46, 175-179, 1997.
Preciado-Patt et al., Eur. J. Biochem. 1994; 223:35-42.
Stein, Am J. Cardiol, 2001; 87(suppl): 21A-26A.
Suzuki et al., J Immunol 2010; 184: 1968-1976.

* cited by examiner

*Primary Examiner* — Christina M Borgeest
(74) *Attorney, Agent, or Firm* — Amster, Rothstein & Ebenstein LLP

(57) ABSTRACT

Isolated SAA peptides, fusion proteins and compositions comprising such are provided as are domain-specific SAA antibodies. Methods of treating sepsis and endotoxemia are also provided.

9 Claims, 9 Drawing Sheets
Specification includes a Sequence Listing.

A. Sequence of synthetic peptides:
(6-mer offsite by 3)

B. Animal survival (%):
(*, P < 0.05)

```
Pm8-1      RAYTDMKEAN
Pm8-2          MKEANWKNSD
Pm8-3              ANWKNSDKYF
Pm8-4                  KNSDKYFHAR
Pm8-5                      DKYFHARGNY
Ph18-1                                              WGRSGKNPNH
Ph18-2                                                  KNPNHFRPEG
Ph18-3                                                      FRPEGLPEKY
Ph8-1      RAYRDNLEAN
Ph8-2          DNLEANYQNA
Ph8-3              ANYQNADQYF
Ph8-4                  NADQYFYARG
```

Fig. 9

SAA-DOMAIN-SPECIFIC ANTIBODIES AND PEPTIDE ANTAGONISTS AND USE THEREOF TO TREAT INFLAMMATORY DISEASES

CROSS-REFERENCE TO RELATED APPLICATIONS

This application is a divisional of U.S. patent application Ser. No. 14/326,710, filed Jul. 9, 2014, which claims benefit of U.S. Provisional Application No. 61/846,749, filed Jul. 16, 2013, the contents of which are hereby incorporated by reference.

STATEMENT OF GOVERNMENT SUPPORT

This invention was made with government support under grant numbers GM063075 and AT005076 awarded by the National Institutes of Health. The government has certain rights in the invention.

BACKGROUND OF THE INVENTION

Throughout this application various publications are referred to in parentheses. Full citations for these references may be found at the end of the specification immediately preceding the claims. The disclosures of these publications, and of all books, patents and patent application publications referred to herein, are hereby incorporated by reference in their entireties into the subject application to more fully describe the art to which the subject application pertains.

Bacterial infection and sepsis are the most common causes of death in the intensive care unit, annually claiming >225,000 victims in the U.S. alone. The pathogenesis of sepsis remains poorly understood, but is attributable to dysregulated systemic inflammation partly mediated by macrophages/monocytes (1, 2). Macrophages/monocytes are equipped with pattern recognition receptors [PRRs, such as the Toll-like receptors (TLRs), TLR2, TLR4, and TLR9] (3-5), and can bind various pathogen-associated molecular patterns (PAMPs, such as bacterial peptidoglycan, endotoxin, and CpG-DNA) (6-9). Consequently, these innate immune cells release a wide array of early proinflammatory cytokines such as TNF, IL-1 and IFN-γ 10-13. Excessive release of early cytokines contributes to the pathogenesis of LSI 12, 14-16. However, the therapeutic windows for these early mediators are relatively narrow (FIG. 1), prompting the search for other "late" proinflammatory mediators that may offer better therapeutic opportunities.

A decade ago, this laboratory made the seminal finding that high mobility group box-1 (HMGB1) was released from macrophages or monocytes in response to exogenous PAMPs (e.g., endotoxin or CpG-DNA) (17, 18) or endogenous cytokines (e.g., TNF or IFN-γ) (17, 19). Upon binding to the receptor for advanced glycation end products (RAGE), TLR2 or TLR4 (20-22), HMGB1 induces the expression of various cytokines, chemokines, and adhesion molecules (20, 21, 23-29). Consequently, extracellular HMGB1 functions as an alarmin signal to alert, recruit and activate innate immune cells (30-34), thereby sustaining rigorous and potentially injurious LSI. During endotoxemia or sepsis (induced by cecal ligation and puncture, CLP), circulating HMGB1 increased to plateau levels between 24-36 h (FIG. 1) (17, 35). This late appearance precedes the onset of animal lethality, and distinguishes HMGB1 from TNF and other early cytokines (36). The pathogenic role of HMGB1 was inferred from the observations that HMGB1-neutralizing antibodies (17, 35, 37) and inhibitors (e.g., tanshinones, ethyl pyruvate, nicotine, stearoyl lysophosphatidylcholine, epigallocatechin-3-gallate, nicotine, choline, GTS-21, and spermine) (17, 38, 39, 39-47) confer protection against lethal endotoxemia and sepsis, even when the first dose of antidote was given 24 h after CLP—a time point when mice had developed clear signs of sepsis, including lethargy, diarrhea, and piloerection. Conversely, administration of exogenous HMGB1 to mice recapitulated many clinical manifestations of sepsis, including fever 48, derangement of intestinal barrier function 49, and tissue injury (50-53). Collectively, these data establish HMGB1 as a critical "late" mediator of sepsis with a wider therapeutic window (36, 54-56) (FIG. 1).

On one hand, early cytokines TNF and IFN-γ can directly stimulate macrophages or monocytes to release HMGB1 (17, 19), thereby contributing to LPS-induced HMGB1 release. On the other hand, these early cytokines also alter the expression of liver-derived APPs, which may then participate in the regulation of HMGB1 release. For instance, TNF, IL-1, IL-6 57, 58 and IFN-γ (58) inhibited the hepatic expression of a negative APP, fetuin-A, which functions as a negative regulator of HMGB1 release during cerebral ischemia (59), endotoxemia and sepsis (58). However, the possible roles of other positive APPs in the regulation of HMGB1 release have not been identified.

In 1976, serum amyloid A (SAA) was first isolated from human serum as a 12 kDa protein (60) that shared identical N-terminal amino acid sequence with the previously characterized 8.5 kDa tissue amyloid A (AA) protein. Subsequently, it was found that exogenous endotoxin (61, 62) or endogenous cytokines (e.g., TNF, IL-1β and IFN-γ) (63-67) can all induce SAA expression in both hepatocytes and extrahepatic cells, such as macrophages/monocytes (68), endothelial cells, smooth muscle cells, adipocytes (69), intestinal epithelial cells (70), and neurons (71, 72). Consequently, circulating SAA levels are dramatically elevated (up to 1000-folds) within 16-24 h of endotoxemia as a result of the de novo expression of early cytokine inducers and the subsequent synthesis of SAAs (61, 73, 74).

Clinically, SAA levels have been regarded as a hallmark/risk factor of many diseases including atherosclerosis (75), cardiovascular diseases (76, 77), Crohn's disease, ulcerative colitis (78), as well as LSI diseases (such as endotoxemia and sepsis) (79-81). Upon secretion, extracellular SAA acts as a chemoattractant for inflammatory cells such as macrophages/monocytes (82-84), T cells (85) and mast cells (86). Furthermore, it activates innate immune cells (e.g., macrophages, monocytes, neutrophils and mast cells) to produce various cytokines and chemokines (e.g., TNF, IL-1β, IL-6, IL-10, GM-CSF, IL-8, MCP-1, MIP-1α, and MIP-3α) (87-94). Finally, SAA stimulates non-immune cells to release other proinflammatory factors such as the group II secretory phospholipase A2 (sPLA2, in smooth muscle cells) (95, 96) and prostaglandins (in endothelial cells) (97). However, it is not known whether SAA occupies an important role in the regulation of HMGB1 release, thereby functioning as an "intermediate" (as opposed to TNF being "early" and HMGB1 being "late") mediators of LSI (FIG. 1).

Extensive studies have revealed distinct functional domains in SAA that are specifically responsible for: 1) SAA secretion (i.e., the signal sequence, D1); 2) HDL binding (D2); 3) cellular adhesion (D3); 4) as-yet-undefined function (D4); 5) protease cleavage (between residues 76-77); and 6) cell activation (D5) (FIG. 2). For instance, the signal sequence directs pro-SAA to the endoplasmic reticulum, and is cleaved prior to extracellular secretion of the mature SAA (98). The α-helical D2 domain serves as the driving force for binding to high density lipoprotein (HDL) (99,100). Within the D2 domain, the first 10-15 residues are particularly critical for the amyloidosis of SAA (101), because deletion or mutation in this region impaired amyloid fibril formation (102, 103). The D3 domain contains YIGSD laminin-related and RGN fibronectin-related motifs, and can inhibit T cell and platelet adhesion to extracellular matrixes (104, 105). At position 76-77 lies a cleavage site for the leukocyte-derived proteases, which break the serine-leucine bond (106-108) to liberate the 8.5-kDa amyloid A (AA) and 3.5-kDa (D5) fragments. The accumulation of the AA precipitates the formation of amorphous amyloid fibril deposits—amyloidosis in peripheral tissues with progressive loss of organ function. On the other hand, the 3.5-kDa fragment may be proinflammatory, because a synthetic peptide corresponding to residues 98-104 stimulates human CD4 T cells to produce IFN-γ (109).

The present invention addresses the need for improved therapies, based on SAA, to combat sepsis and endotoxemia.

SUMMARY OF THE INVENTION

An isolated peptide of 6 to 20 consecutive amino acids is provided comprising (i) 6 to 18 consecutive amino acids of SEQ ID NO:1, (ii) 6 to 18 consecutive amino acids of SEQ ID NO:2, (iii) 6 to 18 consecutive amino acids of SEQ ID NO:3, or (iv) 6 to 18 consecutive amino acids of SEQ ID NO:4.

Also provided is a composition comprising an isolated peptide as described herein and a carrier.

Also provided is a fusion protein comprising an isolated peptide as described herein bonded via a peptide bond at an N-terminal thereof or a C-terminal thereof to a second peptide, polypeptide or protein. An isolated cDNA which encodes a fusion protein as described herein is provided.

Also provided is an isolated antibody directed to a domain of SAA, wherein the antibody cross-reacts with isolated peptide P8 (SEQ ID NO: 2) and/or with isolated peptide P4 (SEQ ID NO:3), or an antigen-binding fragment of such antibody.

An isolated antibody is provided directed to a domain of human SAA, wherein the antibody cross-reacts with isolated peptide P8 (SEQ ID NO:2) or with isolated peptide P4 (SEQ ID NO:3), or with one of isolated peptides SEQ ID NOS: 14-18, or an antigen-binding fragment of such antibody.

A composition is provided comprising an isolated antibody as described herein or antigen-binding fragment of such antibody as described herein, and a carrier.

A hybridoma which produces an isolated antibody as described herein is provided. An isolated cDNA which encodes an isolated antibody as described herein is provided.

A method is provided of treating or preventing sepsis or endotoxemia in a subject, comprising administering to the subject an amount of an isolated peptide as described herein, the fusion protein as described herein, an antibody or fragment thereof as described herein, or a composition as described herein, effective to treat or prevent sepsis or endotoxemia.

A method is provided of treating or preventing an inflammatory condition in a subject, comprising administering to the subject an amount of an isolated peptide as described herein, the fusion protein as described herein, an antibody or fragment thereof as described herein, or a composition as described herein, effective to treat or prevent an inflammatory condition.

Also provided is a peptide having a biological activity of a peptide comprising SEQ ID NO:5, SEQ ID NO:6, SEQ ID NO:7, SEQ ID NO:8 or SEQ ID NO:9, but not comprising SEQ ID NO:5, SEQ ID NO:6, SEQ ID NO:7, SEQ ID NO:8 or SEQ ID NO:9, respectively.

Figure 1:
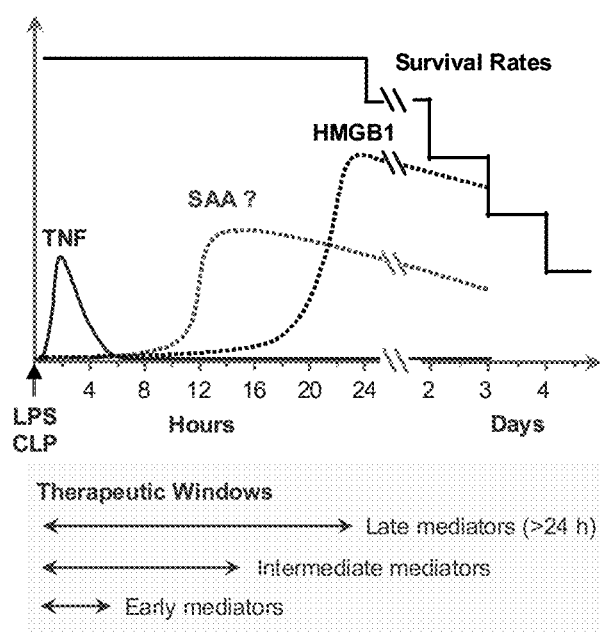
FIG. 1. "Early" versus "late" mediators of lethal systemic inflammation (LSI).
Figure 2:
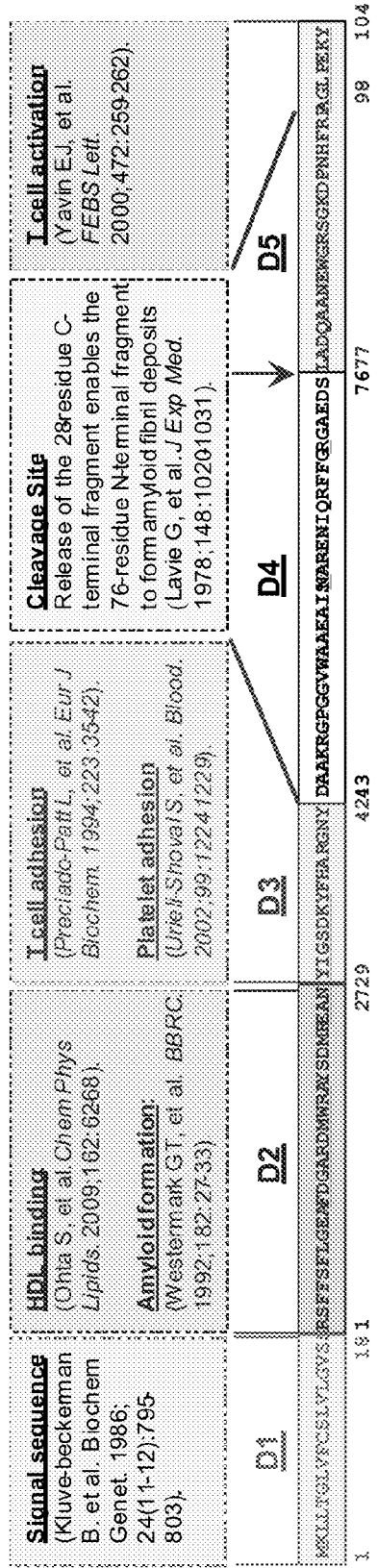
FIG. 2. Functional domains of SAA (SEQ ID NO:18).

REANYIGSDKYFHARGNY, P8 mouse SAA—SEQ ID NO:2 KEANWKNSDKYFHARGNY, P4 human SAA—SEQ ID NO:3 RSFFSFLGEAFDGARDMW, SEQ ID NO:4 GFFSFVHEAFQGAGDMWR, P8-8—SEQ ID NO:5 NSDKYF, P8-7—SEQ ID NO:6 NWKNSD, P8-6—SEQ ID NO:7 KEANWK, P8-4—SEQ ID NO:8 KYFHAR, P8-5—SEQ ID NO:9 HARGNY, P8-1—SEQ ID NO:10 REANYI, P8-2—SEQ ID NO:11 NYIGSD, P8-3—SEQ ID NO:12 GSDKYF).

FIG. 9. Four fusion proteins were constructed that each displayed 3 of the 12 peptides (10-mer, sequences shown, SEQ ID NOS:24-35, top to bottom) on the surface of insoluble and highly immunogenic molecules. These fusion proteins were expressed, purified, and used to immunize mice to generate hybridomas using standard procedures. Hybridoma cell culture supernatants were screened for cross-reactivity with human or murine SAAs, and ability to inhibit SAA-induced release of nitric oxide or G-CSF in macrophage cultures. From top to bottom, sequences are SEQ ID NOS: 18, 19, 20, 13, 14, 21, 16, 17, 22, 23, 15 and 24.

DETAILED DESCRIPTION OF THE INVENTION

An isolated peptide of 6 to 20 consecutive amino acids is provided comprising (i) 6 to 18 consecutive amino acids of SEQ ID NO:1, (ii) 6 to 18 consecutive amino acids of SEQ ID NO:2, (iii) 6 to 18 consecutive amino acids of SEQ ID NO:3, or (iv) 6 to 18 consecutive amino acids of SEQ ID NO:4.

This invention also provides a peptide fragment of SAA which inhibits SAA-induced HMGB1 release in a mammal. This invention also provides a peptide fragment of SAA which inhibits sepsis mortality rates in a population of septic mammals. This invention also provides a peptide fragment of SAA which treats sepsis mortality in a mammal.

The following peptides, and peptides comprising such, are provided:

```
                                    SEQ ID NO: 1
REANYIGSDKYFHARGNY P8 human SAA -

SEQ ID NO: 2
KEANWKNSDKYFHARGNY P8 mouse SAA -

SEQ ID NO: 3
RSFFSFLGEAFDGARDMW P4 human SAA -

SEQ ID NO: 4
GFFSFVHEAFQGAGDMWR -

SEQ ID NO: 5
NSDKYF P8-8 -

SEQ ID NO: 6
NWKNSD P8-7 -

SEQ ID NO: 7
KEANWK P8-6 -

SEQ ID NO: 8
KYFHAR P8-4 -

SEQ ID NO: 9
HARGNY P8-5 -

SEQ ID NO: 10
REANYI P8-1 -

SEQ ID NO: 11
NYIGSD P8-2 -

SEQ ID NO: 12
GSDKYF P8-3 -.
```

The fragments provided are isolated peptides not having the naturally occurring sequence of full length serum amyloid A. Moreover, given the different domain functions of serum amyloid A, as described herein, the peptides comprising less than all the domains described clearly have different characteristics to the naturally-occurring SAA protein (a 12 KDa protein).

In an embodiment, the isolated peptide comprises SEQ ID NO:5, SEQ ID NO:6, SEQ ID NO:7, SEQ ID NO:8 or SEQ ID NO:9. In an embodiment, the isolated peptide comprises SEQ ID NO:5. In an embodiment of the isolated peptide, all the amino acid residues of the peptide are D-amino acids. In an embodiment of the isolated peptide, all the amino acid residues of the peptide are L-amino acids.

The 6 to 20 consecutive amino acid isolated peptide can be any one of 20, 19, 18, 17, 16, 15, 14, 13, 12, 11, 10, 9, 8, 7 or 6 amino acids in length. Each individual peptide length recited herein is encompassed within the invention as an individual embodiment. In addition, each of all the length ranges within the recited lengths is also encompassed within the invention as an individual embodiment. For example, this invention encompasses the isolated peptides of 15-20 amino acids in length, the isolated peptides of 14-20 amino acids in length, the isolated peptides of 14-19 amino acids in length, the isolated peptides of 13-14 amino acids in length and so forth.

In an embodiment, the isolated peptide does not consist of SEQ ID NO:10. In an embodiment, the isolated peptide does not consist of SEQ ID NO:11. In an embodiment, the isolated peptide does not consist of SEQ ID NO:12.

In an embodiment, the isolated peptide comprises SEQ ID NO:5, 6, 7, 8 or 9, and has a sequence as set forth in any of the sequences above except for comprising one or more amino acid substitutions in the isolated peptide that are not in the SEQ ID NO:5, 6, 7, 8 or 9 portion thereof. The isolated peptide may have one of: 80% or greater identity with any one of SEQ ID NO:5, 6, 7, 8 or 9, 85% or greater identity with any one of SEQ ID NO:5, 6, 7, 8 or 9, 90% or greater identity with any one of SEQ ID NO:5, 6, 7, 8 or 9, 95% or greater identity with any one of SEQ ID NO:5, 6, 7, 8 or 9, or 99% identity with any one of SEQ ID NO:5, 6, 7, 8 or 9.

The substitution variants of the invention have at least one amino acid residue in the isolated peptide removed and a different residue inserted in its place. The sites of greatest interest for substitutional mutagenesis are outside the core sequences, i.e. in residues other than SEQ ID:5, 6, 7, 8 or 9. In an embodiment, one or more of the substitutions is a conservative substitution. Conservative substitutions are shown in Table 1 under the heading of "conservative substitutions." In an embodiment, one or more of the substitutions is a substitution as set forth in the third column of Table 1.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Modifications in the biological properties of the isolated peptide are accomplished by selecting substitutions that differ significantly in their effect on maintaining (a) the structure of the polypeptide backbone in the area of the substitution, (b) the charge or hydrophobicity of the molecule at the target site, or (c) the bulk of the side chain. Naturally occurring residues are divided into groups based on common side-chain properties:
(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

In an embodiment, the substitution variants of the invention comprise non-conservative substitutions. Non-conservative substitutions are made by exchanging a member of one of the classes (1) through (6) for another class.

In an embodiment, the substitution or substitutions improve solubility of the isolated peptide in the serum of a subject. In an embodiment, the substitution or substitutions improve the half-life of the isolated peptide in the body of a subject. An improvement is relative to the corresponding non-substituted peptide.

This invention also provides any of the above-described peptides with one substitution or with two substitutions in the sequence SEQ ID NO:5, 6, 7, 8 or 9.

The isolated peptide can comprise both D-amino acids and L-amino acids. In an embodiment, all the amino acid residues of the peptide are D-amino acids. In an embodiment, all the amino acid residues of the peptide are L-amino acids.

Also provided is a fusion protein comprising an isolated peptide as described herein bonded via a peptide bond at an N-terminal thereof or a C-terminal thereof to a second peptide, polypeptide or protein. A fusion protein is provided comprising the isolated peptide as described hereinabove, joined at an N-terminal amino acid or C-terminal amino acid thereof by a peptide bond to a second peptide or polypeptide or protein. In an embodiment, the fusion protein comprising the isolated peptide has a longer half-life in a human subject than the isolated peptide alone does. In an embodiment, the fusion protein comprising the isolated peptide is more soluble in the serum of a human subject than the isolated peptide alone is. In a preferred embodiment, the fusion protein is an isolated recombinant fusion protein created by recombinant DNA technology. In an embodiment, the peptide is fused to a functional domain of a second peptide or polypeptide or protein. In an embodiment, the peptide is fused to a functional domain of a second peptide which is a cell-penetrating peptide. In an embodiment, the cell-penetrating peptide is TAT, transportan or penetratin. In an embodiment, the peptide is fused to an immunoglobulin constant domain (Fc).

In an embodiment, the peptide is fused to a human immunoglobulin constant domain, i.e. a polypeptide having a sequence identical to a human immunoglobulin constant domain but not obtained from an actual human subject. In an embodiment, the isolated peptide is bonded via a peptide bond at an N-terminal thereof or a C-terminal thereof to a immunoglobulin fragment crystallizable region (Fc). In an embodiment, the Fc has a sequence identical to a human Fc.

In an embodiment, the fusion protein comprising the isolated peptide has a longer half-life in a human subject than the isolated peptide alone does. In an embodiment, the fusion protein comprising the isolated peptide is more soluble in the serum of a human subject than the isolated peptide alone is.

In an embodiment, "isolated" as used herein means not naturally occurring without the hand of man.

Also provided is a composition comprising an isolated peptide as described herein and a carrier. Also provided is a composition comprising a fusion protein as described herein and a carrier. The invention encompasses compositions comprising the isolated peptides described herein or the fusion proteins described herein. In an embodiment, the composition is a pharmaceutical composition. In an embodiment the composition or pharmaceutical composition comprising one or more of the isolated peptides described herein or the fusion proteins described herein is substantially pure with regard to the isolated peptides described herein or the fusion proteins described herein. A composition or pharmaceutical composition comprising one or more of the isolated peptides described herein or the fusion proteins described herein is "substantially pure" with regard to that when at least 60% of a sample of the composition or pharmaceutical composition exhibits a single species of the isolated peptide or fusion protein. A substantially pure composition or pharmaceutical composition comprising one or more of the isolated peptides described herein or the fusion proteins described herein can comprise, in the portion thereof which is the isolated peptide or fusion protein, 60%, 70%, 80% or 90% of the isolated peptide or fusion protein of the single species, more usually about 95%, and preferably over 99%. Purity or homogeneity may tested by a number of means well known in the art, such as polyacrylamide gel electrophoresis or HPLC.

In an embodiment, the composition is a dimer or trimer of the isolated peptides. In an embodiment, the composition is a dimer or trimer of the fusion proteins.

Compositions or pharmaceutical compositions disclosed herein preferably comprise stabilizers to prevent loss of activity or structural integrity of the peptide or fusion protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH of 6.8 to 7.4.

In an embodiment the isolated peptides or fusion proteins disclosed herein are lyophilized and/or freeze dried and are reconstituted for use.

The invention encompasses compositions comprising the isolated peptides or fusion proteins described herein in a pharmaceutically acceptable carrier. As used herein, "pharmaceutically acceptable carrier" includes any material (including mixtures) which, when combined with an active ingredient, allows the ingredient to retain biological activity and is non-reactive with the subject's immune system. Examples include, but are not limited to, any of the standard pharmaceutical carriers such as one or more of phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000). In non-limiting examples, the can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxy ethoxy)ethoxy]ethyl (E)-octadec-9-enoate), disodium edetate dehydrate, sucrose, monobasic sodium phosphate monohydrate, and dibasic sodium phosphate dihydrate.

The compositions or pharmaceutical compositions described herein can also be lyophilized or provided in any suitable forms including, but not limited to, injectable solutions or inhalable solutions, gel forms and tablet forms.

The practice of the present invention can employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997).

In some embodiments, therapeutic administration of the isolated peptide, or of the composition comprising such, advantageously results in reduced incidence and/or amelioration of one or more symptoms of the sepsis or endotoxemia condition. In an embodiment, the said composition is a pharmaceutical composition. In some embodiments, therapeutic administration of the isolated fusion-protein or the composition comprising such advantageously results in reduced incidence and/or amelioration of one or more symptoms of the sepsis or endotoxemia condition. In an embodiment, the said composition is a pharmaceutical composition.

With respect to the therapeutic methods described herein, reference to compositions includes compositions comprising one or more additional agents, unless otherwise indicated. These compositions may further comprise suitable excipients, such as pharmaceutically acceptable excipients including buffers, which are well known in the art. The present invention can be used alone or in combination with other methods of treatment. In an embodiment, the other method of treatment comprise an anti-inflammation therapy and/or an anti-bacterial therapy.

The isolated peptides, fusion proteins, or compositions comprising such, can be administered to an subject via any suitable route. It should be apparent to a person skilled in the art that the examples described herein are not intended to be limiting but to be illustrative of the techniques available. Accordingly, in some embodiments, the they are administered to a subject in accord with known methods, such as intravenous administration, e.g., as a bolus or by continuous infusion over a period of time, by intramuscular, intraperitoneal, intracerebrospinal, transdermal, subcutaneous, intraarticular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution.

In some embodiments, the isolated peptide, fusion protein, or composition comprising such, is administered via site-specific or targeted local delivery techniques. Examples of site-specific or targeted local delivery techniques include various implantable depot sources or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of the isolated peptide or fusion protein of the invention may be used for administration. In some embodiments, the isolated peptide or fusion protein of the invention may be administered neat. In some embodiments, the isolated peptide or fusion protein of the invention and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular subject and that subject's medical history.

Therapeutic formulations of the peptide or fusion protein used in accordance with the present invention are prepared for storage by mixing with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the peptide or fusion protein are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the isolated peptide or fusion protein, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Emulsion compositions of the invention can be those prepared by mixing an isolated peptide or fusion protein of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Also provided is an isolated antibody directed to a domain of SAA, wherein the antibody cross-reacts with isolated peptide P8 (SEQ ID NO: 2) and/or with isolated peptide P4 (SEQ ID NO:3), or an antigen-binding fragment of such antibody.

Also provided is an isolated antibody directed to a domain of human SAA, wherein the antibody cross-reacts with isolated peptide P8 (SEQ ID NO:2) or with isolated peptide P4 (SEQ ID NO:3), or with one of isolated peptides SEQ ID NOS: 13-17, or an antigen-binding fragment of such antibody.

In an embodiment, the isolated antibody reacts with one of amino acid sequences ANYQNADQYF (SEQ ID NO:15), DKYFHARGNY (SEQ ID NO:14), or FRPEGLPEKY (SEQ ID NO:17). In an embodiment, the isolated antibody reacts with amino acid sequence KNPNHFRPEG (SEQ ID NO:16).

In an embodiment, the isolated antibody is non-naturally occurring in that it does not exist absent the hand of man in its production.

In an embodiment, the isolated antibody inhibits SAA-induced nitric oxide production when applied to a human macrophage culture. In an embodiment, the isolated antibody inhibits SAA-induced G-CSF production when applied to a human macrophage culture.

In a preferred embodiment, the antibody cross-reacts with isolated peptide P8 (SEQ ID NO: 2). In a preferred embodiment, the antibody does not bind an epitope bound by monoclonal antibody mc29 and/or wherein the antibody does not bind an epitope bound by monoclonal antibody mc4.

In an embodiment, the antibody is a monoclonal antibody. In an embodiment, the antibody is a chimeric antibody, humanized antibody or human antibody.

A composition is provided comprising an isolated antibody as described herein or antigen-binding fragment of such antibody as described herein, and a carrier.

As used herein, the term "antibody" refers to an intact antibody, i.e. with complete Fc and Fv regions. "Fragment" refers to any portion of an antibody, or portions of an antibody linked together, such as, in non-limiting examples, a Fab, F(ab)$_2$, a single-chain Fv (scFv), which is less than the whole antibody but which is an antigen-binding portion and which competes with the intact antibody, of which it is a fragment, for specific binding. As such, a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, F$_d$, F$_v$, complementarity determining region (CDR) fragment, single-chain antibody (scFv), (a variable domain light chain (V$_L$) and a variable domain heavy chain (V$_H$) linked via a peptide linker. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer SAA domain-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342: 878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an F$_d$ fragment means an antibody fragment that consists of the V$_H$ and CH1 domains; an F$_v$ fragment consists of the V$_1$ and V$_H$ domains of a single arm of an antibody; and a dAb fragment (Ward et al., Nature 341:544-546 (1989) hereby incorporated by reference in its entirety) consists of a V$_H$ domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target SAA domain, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

In an embodiment of the inventions described herein, the antibody is isolated. As used herein, in an embodiment, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not naturally occur absent the hand of man.

In an embodiment the composition or pharmaceutical composition comprising one or more of the antibodies or fragments described herein is substantially pure with regard to the antibody or fragment. A composition or pharmaceutical composition comprising one or more of the antibodies or fragments described herein is "substantially pure" with regard to the antibody or fragment when at least about 60 to 75% of a sample of the composition or pharmaceutical composition exhibits a single species of the antibody or fragment. A substantially pure composition or pharmaceutical composition comprising one or more of the antibodies or fragments described herein can comprise, in the portion thereof which is the antibody or fragment, 60%, 70%, 80% or 90% of the antibody or fragment of the single species, more usually about 95%, and preferably over 99%. Antibody purity or homogeneity may tested by a number of means well known in the art, such as polyacrylamide gel electrophoresis or HPLC.

As used herein, a "human antibody" unless otherwise indicated is one whose sequences correspond to (i.e. are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (e.g. Hoogenboom and Winter, J. Mol. Biol., 227:381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147(1):86-95 (1991) (hereby incorporated by reference in its entirety), van Dijk and van de Winkel, Curr. Opin. Pharmacol., 5: 368-74 (2001) (hereby incorporated by reference in its entirety), and by administering the antigen to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entirety), e.g. VelocImmune® (Regeneron, Tarrytown, N.Y.), e.g. Ulti-Mab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto other than antibodies naturally occurring in a human or made in a human. Furthermore, if the antibody (e.g. an intact antibody rather than, for example, an Fab fragment) contains a constant region, the constant region also is derived from such human sequences, e.g., human germline sequences, or mutated versions of human germline sequences. However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

In an embodiment, the anti-SAA antibody described herein is a recombinant human antibody. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the anti-SAA antibody described herein is capable of specifically binding or specifically binds an SAA domain. As used herein, the terms "is capable of specifically binding" or "specifically binds" refers to the property of an antibody or fragment of binding to the (specified) antigen with a dissociation constant that is <1 µM, preferably <1 nM and most preferably <10 pM. In an embodiment, the Kd of the antibody (or fragment) for SAA is 250-500 pM. An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include, in an embodiment) exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the $V_H$ (H1, H2, H3) and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy) oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

A hybridoma is provided which produces an antibody as described herein.

An isolated cDNA is provided which encodes an antibody as described herein.

An isolated cDNA is provided which encodes a fusion protein as described herein.

The methods of routes of administration described hereinabove with regard to peptides are also applicable to the antibodies, antibody fragments, and compositions comprising either as described herein.

A method is provided of treating or preventing sepsis or endotoxemia in a subject, comprising administering to the subject an amount of an isolated peptide as described herein, the fusion protein as described herein, an antibody or fragment thereof as described herein, or a composition as described herein, effective to treat or prevent sepsis or endotoxemia.

A method is provided of treating or preventing an inflammatory condition in a subject, comprising administering to the subject an amount of an isolated peptide as described herein, the fusion protein as described herein, an antibody or fragment thereof as described herein, or a composition as described herein, effective to treat or prevent an inflammatory condition.

In an embodiment, the methods further comprise administering an amount of exogenous HDL to the subject sufficient to reduce plasma levels of SAA in a subject.

In an embodiment of the methods, the antibody or fragment, or the composition comprising such, is administered. In an embodiment, the isolated peptide, or the fusion protein or composition comprising such, is administered.

In an embodiment of the methods herein, the isolated peptide, fusion protein, antibody or composition is administered to the subject prior to the onset of sepsis or endotoxemia, for example, to a subject at risk for sepsis. In an embodiment of the methods herein, the isolated peptide, fusion protein, antibody or composition is administered to the subject after the onset of sepsis or endotoxemia or inflammatory condition, for example, within 2 hrs., 5 hrs., 10 hrs., 24 hrs. or 48 hrs. or more after the onset of sepsis or endotoxemia or inflammatory condition. In an embodiment of the methods herein, the isolated peptide, fusion protein, antibody or composition is administered to the subject showing sepsis symptoms or showing endotoxemia symptoms or exhibiting the inflammatory condition.

Also provided is a peptide having a biological activity of a peptide comprising SEQ ID NO:5, SEQ ID NO:6, SEQ ID NO:7, SEQ ID NO:8 or SEQ ID NO:9, but not comprising SEQ ID NO:5, SEQ ID NO:6, SEQ ID NO:7, SEQ ID NO:8 or SEQ ID NO:9, respectively.

In an embodiment of any of the peptides described herein, the peptide attenuates SAA-induced HMGB1 release from a cell, or in a subject. In an embodiment of any of the antibodies or fragments described herein, the antibody or fragment attenuates SAA-induced HMGB1 release from a cell, or in a subject.

The term "subject" is intended to include mammals, e.g., humans, dogs, cows, horses, pigs, sheep, goats, cats, mice, rabbits, rats, and also includes avians. In a preferred embodiment of the invention, the subject is a human.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Despite recent advances in antibiotic therapy and intensive care, bacterial infection and sepsis remain widespread problems in critically ill patients. The high mortality of sepsis is partly mediated by bacterial toxins, which stimulate macrophages/monocytes to sequentially release early (e.g., TNF and IFN-γ) and late (e.g., HMGB1 and histones) proinflammatory mediators. Anti-TNF agents can be protective in animal models of endotoxemic shock if given prophylactically; whereas agents capable of inhibiting HMGB1 release or activities rescue mice from lethal sepsis even when these anti-HMGB1 agents are first given 24 h after disease onset. To search for other HMGB1 regulators, we systematically monitored the dynamic changes of the circulating levels of HMGB1 and multiple other cytokines/chemokines in septic patients by Western blots and Antibody Arrays. Intriguingly, a positive APP, human serum amyloid A (SAA), but not SAA1, cross-reacted with some rabbit anti-HMGB1 antibodies, and surprisingly induced HMGB1 release in murine macrophage and human monocyte cultures. Furthermore, recombinant SAA protein exacerbated endotoxin-mediated animal lethality; whereas SAA domain-specific neutralizing antibodies and peptide antagonists conferred protection against lethal endotoxemia and sepsis.

Results

Figures 3A, 3B, 3C, 3D:
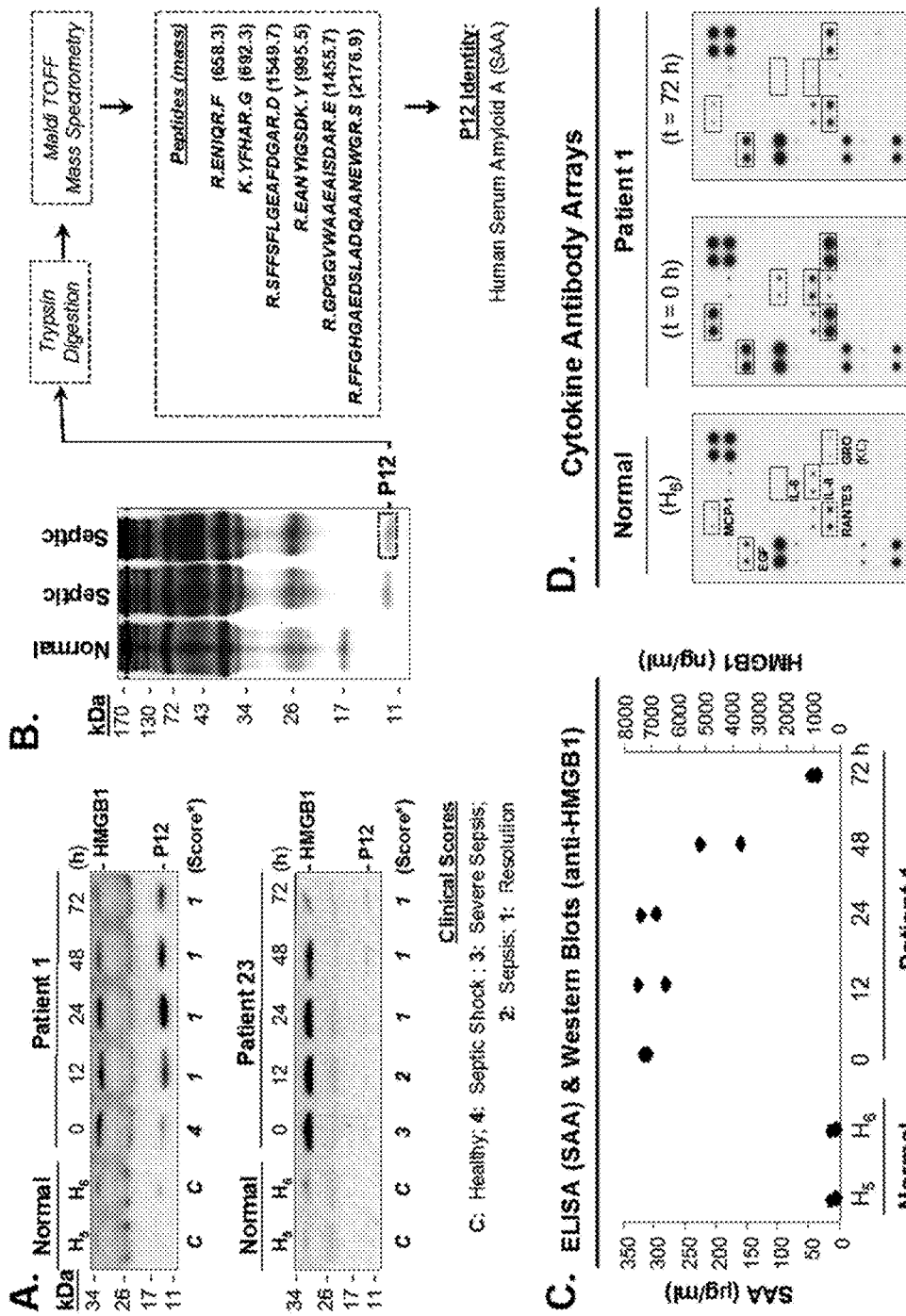
FIG. 3A-3D. Identification of SAA as an anti-HMGB1 IgG-cross-reacting protein in septic patients. A, Western blots of serum proteins. Note that anti-HMGB1 IgGs recognized both the 30 kDa HMGB 1 and a 12 kDa protein (termed "P12") in septic patients. B, Mass spectrometry analysis of P12 (SEQ ID NOS:36-41, top to bottom, respectively). C, D, Immunoassays of total SAAs and multiple other cytokines by ELISA and Cytokine Antibody Arrays. Note that serum HMGB1 levels positively correlated with SAAs and several sepsis surrogate markers.

Discovery of human SAA, but not SAA1, as an HMGB1 inducer. To search for potential "intermediate" mediators that could contribute to HMGB1 release, the kinetic changes of serum levels of HMGB1 along with multiple other cytokines in a group of septic patients admitted to the NSUH were characterized subsequent to the approval by the institutional IRB ethics committee. In 8 out of 23 septic patients, serum HMGB1 levels positively correlated with the clinical scores—circulating HMGB1 levels returned to baselines when these patients recovered from the illness (110). In a subset of septic patients, some anti-HMGB1 IgGs paradoxically cross-reacted with a 12 kDa protein (denoted as "P12") (FIG. 3A), which was identified as a member of the human SAA family by mass spectrometry analysis (FIG. 3B). Furthermore, serum HMGB1 levels appeared to positively correlate with the serum levels of total SAAs (as measured by ELISA, FIG. 3C), several sepsis surrogate markers (e.g., IL-6, GRO/KC, IL-8, MCP-1, and RANTES), as well as a cytoprotective peptide, EGF (41, 111-114) (FIG. 3D). However, most of these inflammatory mediators (e.g., IL-6, IL-8, EGF and KC) were unable to induce HMGB1 release in vitro (data not shown), eliminating their potential involvement in the regulation of HMGB1 release during sepsis.

Figures 4A, 4B, 4C:
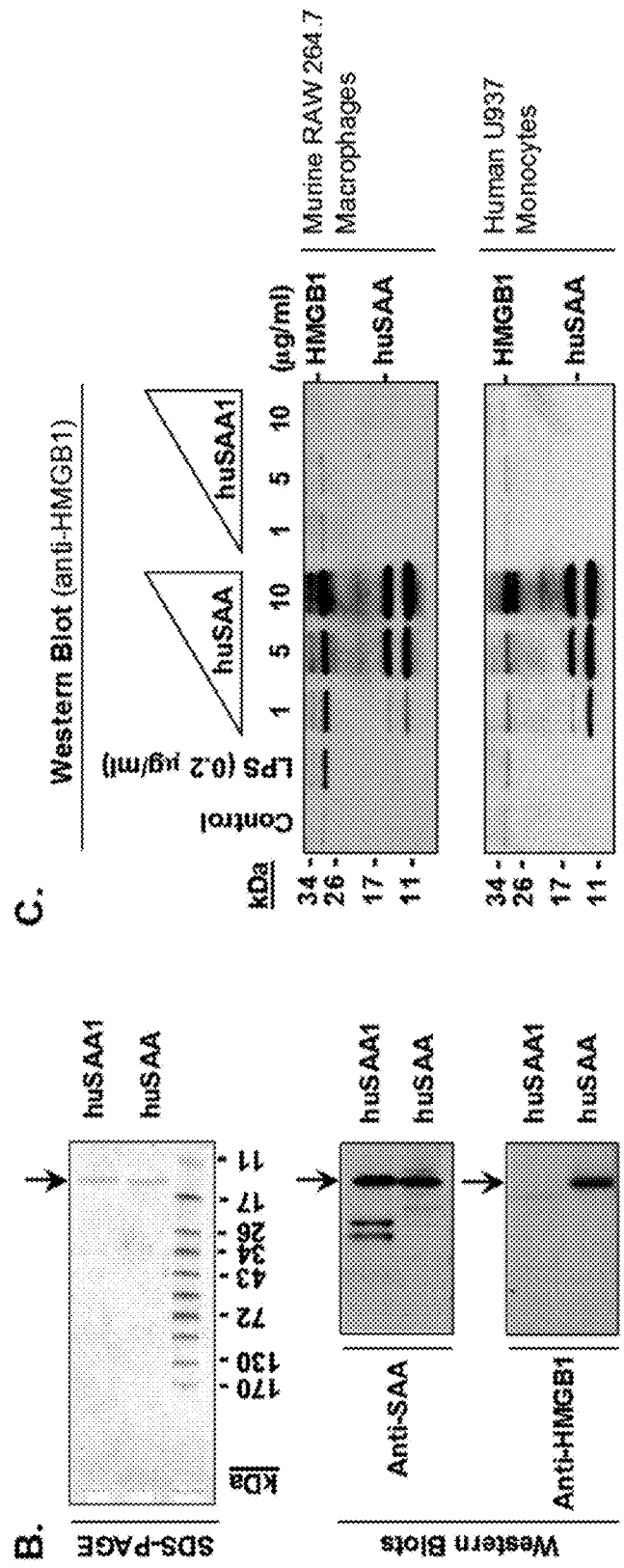
FIG. 4A-4C. Human SAA, but not SAA1, induced HMGB1 release in vitro. A, Amino acid sequence of human and murine SAAs (SEQ ID NOS:19-23, top to bottom). B, Western blots of human SAA and SAA1. Note that the anti-HMGB1 IgGs paradoxically cross-reacted with huSAA, but not huSAA1. C, HuSAA, but not huSAA1, induced HMGB1 release. Murine macrophages and human monocytes were stimulated with huSAA or huSAA1 for 16 h, and extracellular HMGB 1 levels were determined by Western blots.

Overall, there is a >95-98% amino acid sequence homology between members of the human or murine SAA families, and a >75% identity across human and murine families (FIG. 4A), making it seemingly difficult to distinguish between different SAA members by immunoassays. Indeed, the polyclonal antibodies raised against human SAA cross-reacted with both human SAA and SAA1 on Western blots (FIG. 4B, bottom panel). Intriguingly, our rabbit anti-HMGB1 IgGs "specifically" recognized human SAA, but not SAA1, on Western blots (FIG. 4B), implicating a possibility of selectively immunodetecting human SAA with appropriate antibodies. Despite the overwhelming sequence identity between human SAA and SAA1 (FIG. 4A), their capacities in stimulating HMGB1 release were surprisingly distinct. At physiologically relevant concentrations (1-10 µg/ml), human SAA (Cat. No. 300-13, PeproTech) effectively induced HMGB1 release in both murine macrophage and human monocyte cultures (FIG. 4C). In a sharp contrast, human SAA1 (Cat. No. 300-53, PeproTech) barely triggered HMGB1 release when given at essentially comparable concentrations (FIG. 4C).

Figures 5A, 5B, 5C:
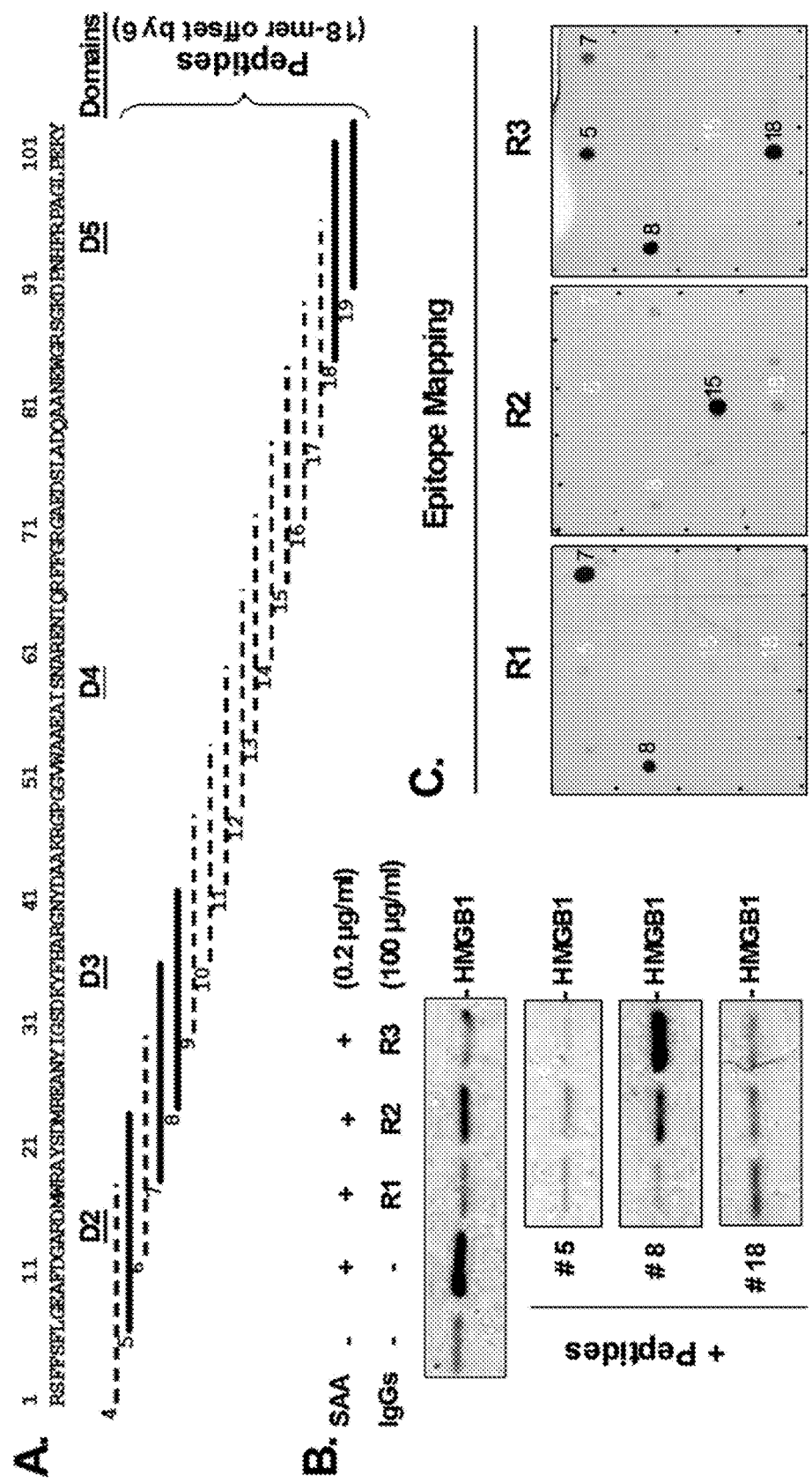
FIG. 5A-5C. Epitope mapping of SAA-specific antibodies using a peptide library. A, Sequence of synthetic SAA peptides (SEQ ID NO:19). B, Effects of anti-SAA IgGs on SAA-induced HMGB1 release. Macrophages were stimulated with SAA in the absence or presence of different (R1, R2, R3) IgGs, and HMGB1 release was assayed by Western blotting. C, Epitope mapping by dot blot. Note that all rabbit IgGs capable of protecting against lethal endotoxemia cross-reacted with P8 peptide.

Epitope mapping of SAA-neutralizing antibodies. To test the possibility that antibodies or peptides antagonists targeting different SAA domains may divergently affect the outcomes of LSI, SAA-specific antibodies were generated, and the epitopes of these polyclonal IgGs determined using a peptide library (18-mer offset by 6) spanning the entire SAA protein (FIG. 5A). Consistent with recent reports that SAA autoantibodies were detected in both healthy individuals and patients with various autoimmune diseases (115, 116), it was found that all rabbits produce small amounts of anti-SAA autoantibodies (immunoreactive to human SAA and, fortunately, not to murine SAA) prior to SAA immunization. Following repetitive immunizations, the titers of anti-SAA IgGs were dramatically elevated in most rabbits (e.g., R1 and R3). Notably, some SAA-specific antibodies significantly attenuated SAA-induced HMGB1 release in vitro (FIG. 5B), whereas the anti-SAA-IgG-mediated inhibition was impaired by pre-incubation with the P8 peptide (FIG. 5B). Interestingly, these SAA-neutralizing antibodies all cross-reacted with the P8 peptide (FIG. 5C), suggest the importance of domain specific neutralizing antibodies to inhibit SAA-induced HMGB1 release.

Figures 6A, 6B, 6C:
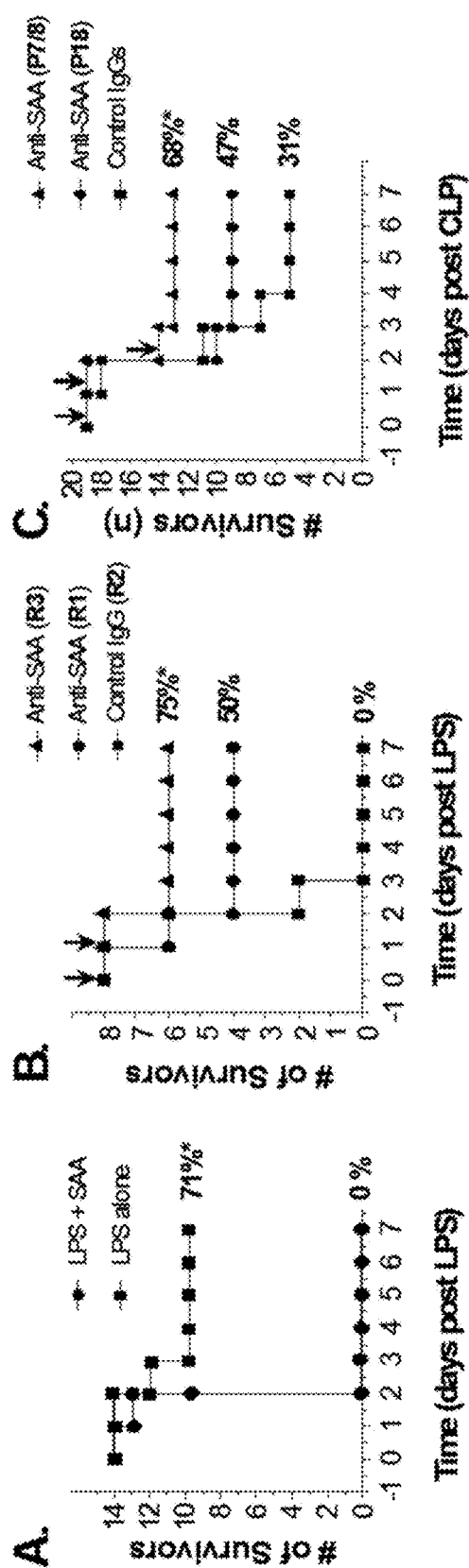
FIG. 6A-6C. Divergent effects of SAA and SAA-neutralizing IgGs on LSI. A, SAA exacerbated LPS-induced animal lethality. Balb/C mice were given LPS (5 mg/kg, i.p.) either alone or in combination with SAA (0.8 mg/kg) to determine their effects on animal survival rates. B, SAA-specific IgGs protected mice against lethal endotoxemia. Balb/C mice were given LPS (15 mg/kg) in combination with either control IgGs (50 mg/kg, R2) or SAA-reacting IgGs (R1 and R3, 50 mg/kg). C, peptide-specific anti-SAA IgGs rescued mice from lethal sepsis. Balb/C mice were subjected to sepsis by CLP, and irrelevant ("control", 50 mg/kg) or SAA peptide-specific IgGs (50 mg/kg) were given at +6, +24, and +48 h post CLP. Shown in the figure is a summary of two independent experiments with similar results.

Anti-SAA antibodies protected mice against lethal endotoxemia and sepsis. To understand the role of SAA in lethal systemic inflammatory diseases, the effect of SAA supplementation or inhibition on animal survival was examined in animal models of lethal endotoxemia and sepsis. Recombinant SAA protein dramatically exacerbated LPS-induced animal lethality (FIG. 6A), whereas repetitive administration of SAA-neutralizing IgGs (at +0.5 and +24 h after LPS) promoted a significant protection against lethal endotoxemia (FIG. 6B). Moreover, polyclonal IgGs targeting specific SAA domains (e.g., the P7/P8 peptides) conferred significant protection in a clinically relevant animal model of CLP-induced sepsis (FIG. 6C), suggesting that dampening undesired SAA functions may be beneficial during LSI. Since "early" (such as TNF) and possibly even "intermediate" (such as SAA) cytokines may still be required for the early innate immunity against infection, the abolition of the SAA-mediated early host defense might still be detrimental (117). Indeed, combinational administration of two MAbs (mc29 and mc4; 1:1), given (50 mg/kg) prophylactically at 12 h before, and additionally (33 mg/kg) at 12 h after, CLP, adversely reduced animal survival rates from 60% to 20% (118).

Figure 7:
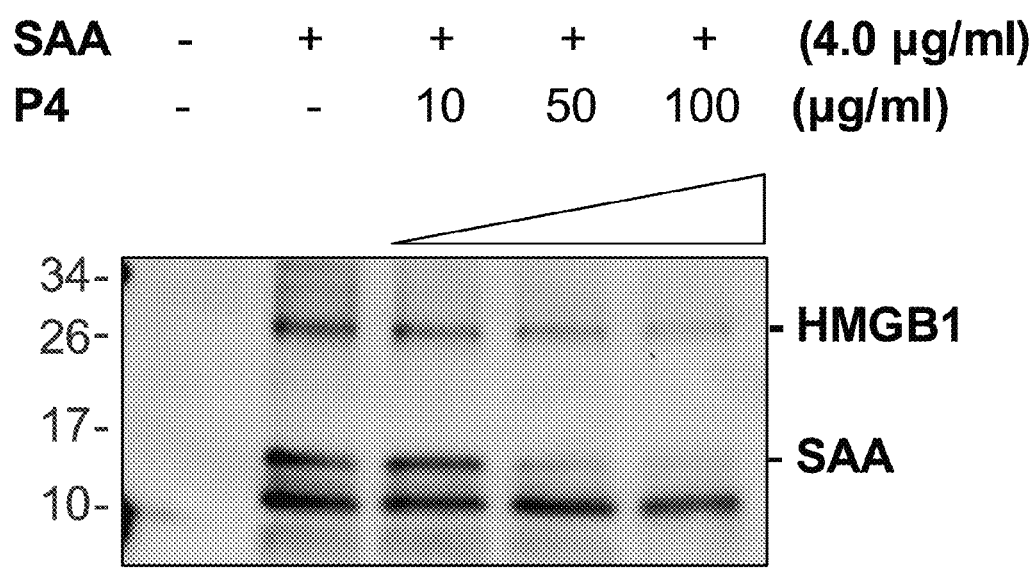
FIG. 7. SAA peptide (P4) inhibited SAA-induced HMGB1 release. P4 peptide corresponded to residues 1-18 that are critical for HDL binding and amyloidosis.

To gain insight into the mechanism of SAA action, the capacities of various SAA peptides was also explored in their effect on SAA-induced HMGB1 release. Consistent with a previous report that a peptide corresponding to residues 98-104 induced IFN-γ production in T cells (109), it was found that a peptide corresponding to residues 85-102 (i.e., the "P18" peptide; 50 µg/ml) elevated SAA (100 ng/ml)-induced HMGB1 release by 2-3 folds. In a sharp contrast, several peptides corresponding to residues 1-18 (the "P4" peptide, FIG. 7) or 25-42 (the "P8" peptide, data not shown) dose-dependently inhibited SAA-induced HMGB1 release, suggesting that selective SAA domain-specific peptides may be developed as antagonists to block SAA-mediated HMGB1 release.

Figure 8:
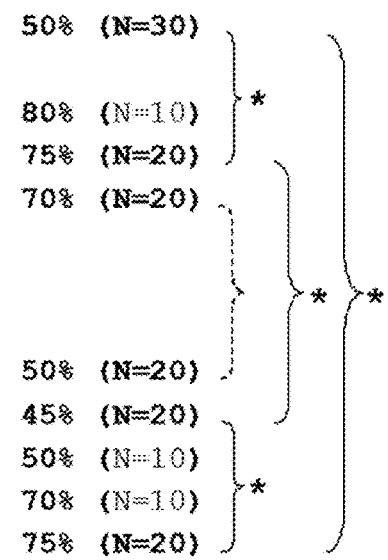
FIG. 8. Effects of SAA peptides on septic animal survival. Various peptides (6-mers) corresponding to the P8 peptide (18-mer) of the human SAA ("HuSAA") or murine SAA1 ("MuSAA1") protein were synthesized (AnaSpec Inc.), and tested for efficacy in animal model of CLP-induced sepsis. At +20 and +48 h post CLP, mice were administered with either saline (i.p., 0.2 ml/mouse) or each peptide (30 mg/kg), and animal survival rates were monitored for two weeks. Shown in the figure is a summary of 2 independent experiments with similar results. (P8 human SAA—SEQ ID NO:1

To explore the therapeutic potential of SAA peptides, a peptide library was synthesized that spanned a smaller region of SAA. Notably, several smaller peptides specifically corresponding to the murine SAA1 (but not human SAA) P8 peptide antagonist significantly rescued mice from lethal sepsis even when the first dose of peptides were given at 20 h post the onset of sepsis (FIG. 8).

Generation and screening SAA peptide-reacting monoclonal antibodies: four fusion proteins were constructed that each displayed of the 12 peptides shown in FIG. 9. (10-mer sequences shown) on the surface of insoluble and highly immunogenic molecules. These fusion proteins were expressed, purified, and used to immunize mice to generate hybridomas using standard procedures. Hybridoma cell culture supernatants were screened for cross-reactivity with human or murine SAAs, and ability to inhibit SAA-induced release of nitric oxide or G-CSF in macrophage cultures. The data obtained is summarized in the Table 2.

TABLE 2

Characterization of mouse anti-SAA peptide hybridomas.

| | | Peptide | Reactivity | | SAA-neutralizing Activity | |
| --- | --- | --- | --- | --- | --- | --- |
| Clone # | Name | Sequence | HuSAAs | MuSAAs | ↓ Nitric Oxide | ↓ G-CSF |
| 8 | Pnn8-4 | KNSDKYFHAR (SEQ ID NO: 13) | – | ++ | 75% | – |
| 9 | Pnn8-5 | DKYFHARGNY (SEQ ID NO: 14) | + | – | | |
| 20 | Ph8-3 | ANYQNADQYF (SEQ ID NO: 15) | + | ++ | 77% | + |
| 22 | Ph8-3 | ANYQNADQYF (SEQ ID NO: 15) | + | + | | |
| 30 | Pnn8-5 | DKYFHARGNY (SEQ ID NO: 14) | ++ | – | 89% | ++ |

TABLE 2-continued

Characterization of mouse anti-SAA peptide hybridomas.

| Clone # | Peptide Name | Peptide Sequence | Reactivity HuSAAs | Reactivity MuSAAs | SAA-neutralizing Activity ↓ Nitric Oxide | ↓ G-CSF |
|---|---|---|---|---|---|---|
| 31 | Ph18-2 | KNPNHFRPEG (SEQ ID NO: 16) | ++ | + | 81% | |
| 32 | Ph18-2 | KNPNHFRPEG (SEQ ID NO: 16) | ++ | +++ | | |
| 34 | Ph18-2 | KNPNHFRPEG (SEQ ID NO: 16) | + | + | 84% | − |
| 35 | Ph18-3 | FRPEGLPEKY (SEQ ID NO: 17) | +++ | ++ | | |
| 36 | Ph18-3 | FRPEGLPEKY (SEQ ID NO: 17) | ++ | + | | |
| 38 | Ph18-3 | FRPEGLPEKY (SEQ ID NO: 17) | + | +++ | 81% | ++ |
| 39 | Ph18-3 | FRPEGLPEKY (SEQ ID NO: 17) | + | − | | |

REFERENCES

1. Hotchkiss, R. S., Coopersmith, C. M., McDunn, J. E. & Ferguson, T. A. The sepsis seesaw: tilting toward immunosuppression. *Nat. Med.* 15, 496-497 (2009).
2. Koay, M. A. et al. Macrophages are necessary for maximal nuclear factor-kappa B activation in response to endotoxin. *Am. J. Respir. Cell Mol. Biol.* 26, 572-578 (2002).
3. Brightbill, H. D. et al. Host defense mechanisms triggered by microbial lipoproteins through toll-like receptors. *Science* 285, 732-736 (1999).
4. Poltorak, A. et al. Defective LPS signaling in C3H/HeJ and C57BL/10 ScCr mice: mutations in Tlr4 gene. *Science* 282, 2085-2088 (1998).
5. Hemmi, H. et al. A Toll-like receptor recognizes bacterial DNA. *Nature* 408, 740-745 (2000).
6. Zingarelli, B. Peptidoglycan is an important pathogenic factor of the inflammatory response in sepsis. *Crit Care Med.* 32, 613-614 (2004).
7. Akira, S. & Takeda, K. Toll-like receptor signalling. *Nat. Rev. Immunol.* 4, 499-511 (2004).
8. Baggiolini, M. & Loetscher, P. Chemokines in inflammation and immunity. *Immunol. Today* 21, 418-420 (2000).
9. Balkwill, F. Cytokines—soluble factors in immune responses. *Curr. Opin. Immunol.* 1, 241-249 (1988).
10. Wang, H., Czura C. J. & Tracey K. J. The Cytokine Handbook. Thomson, A. & Lotze, M. T. (eds.), pp. 837-860 (Academic Press, Oξφορδ, 2003).
11. Dinarello, C. A. Biologic basis for interleukin-1 in disease. *Blood* 87, 2095-2147 (1996).
12. Heinzel, F. P. The role of IFN-gamma in the pathology of experimental endotoxemia. *J. Immunol* 145, 2920-2924 (1990).
13. Varma, T. K., Lin, C. Y., Toliver-Kinsky, T. E. & Sherwood, E. R. Endotoxin-induced gamma interferon production: contributing cell types and key regulatory factors. *Clin. Diagn. Lab Immunol.* 9, 530-543 (2002).
14. Tracey, K. J. et al. Anti-cachectin/TNF monoclonal antibodies prevent septic shock during lethal bacteraemia. *Nature* 330, 662-664 (1987).
15. Dinarello, C. A. & Thompson, R. C. Blocking IL-1: interleukin 1 receptor antagonist in vivo and in vitro. *Immunol Today* 12, 404-410 (1991).
16. Romero, C. R. et al. The role of interferon-gamma in the pathogenesis of acute intra-abdominal sepsis. *J. Leukoc. Biol.* 88, 725-735 (2010).
17. Wang, H. et al. HMG-1 as a late mediator of endotoxin lethality in mice. *Science* 285, 248-251 (1999).
18. Ivanov, S. et al. A novel role for HMGB1 in TLR9-mediated inflammatory responses to CpG-DNA. *Blood* 110, 1970-1981 (2007).
19. Rendon-Mitchell, B. et al. IFN-gamma Induces High Mobility Group Box 1 Protein Release Partly Through a TNF-Dependent Mechanism. *J Immunol* 170, 3890-3897 (2003).
20. Park, J. S. et al. Involvement of TLR 2 and TLR 4 in cellular activation by high mobility group box 1 protein (HMGB1). *J Biol Chem.* 279, 7370-7377 (2004).
21. Yu, M. et al. HMGB1 SIGNALS THROUGH TOLL-LIKE RECEPTOR (TLR) 4 AND TLR2. *Shock* 26, 174-179 (2006).
22. Dai, S. et al. Extracellular high mobility group box-1 (HMGB1) inhibits enterocyte migration via activation of Toll-like receptor-4 and increased cell-matrix adhesiveness. *J. Biol. Chem.* 285, 4995-5002 (2010).
23. Park, J. S. et al. High mobility group box 1 protein interacts with multiple Toll-like receptors. *Am. J. Physiol Cell Physiol* 290, C917-C924 (2006).
24. Kokkola, R. et al. RAGE is the Major Receptor for the Proinflammatory Activity of HMGB1 in Rodent Macrophages. *Scand. J. Immunol* 61, 1-9 (2005).
25. Pedrazzi, M. et al. Selective proinflammatory activation of astrocytes by high-mobility group box 1 protein signaling. *J. Immunol.* 179, 8525-8532 (2007).
26. Yamoah, K. et al. High-mobility group box proteins modulate tumor necrosis factor-alpha expression in osteo- 26. clastogenesis via a novel deoxyribonucleic acid sequence. *Mol. Endocrinol.* 22, 1141-1153 (2008).
27. Fiuza, C. et al. Inflammation-promoting activity of HMGB1 on human microvascular endothelial cells. *Blood* 101, 2652-2660 (2003).
28. Treutiger, C. J. et al. High mobility group 1 B-box mediates activation of human endothelium. *J Intern. Med* 254, 375-385 (2003).
29. Lv, B. et al. High-mobility group box 1 protein induces tissue factor expression in vascular endothelial cells via activation of NF-kappaB and Egr-1. *Thromb. Haemost* 102, 352-359 (2009).
30. Yang, D. et al. High mobility group box-1 protein induces the migration and activation of human dendritic cells and acts as an alarmin. *J. Leukoc. Biol.* 81, 59-66 (2007).
31. Dumitriu, I. E., Bianchi, M. E., Bacci, M., Manfredi, A. A. & Rovere-Querini, P. The secretion of HMGB1 is required for the migration of maturing dendritic cells. *J. Leukoc. Biol.* 81, 84-91 (2007).
32. Orlova, V. V. et al. A novel pathway of HMGB1-mediated inflammatory cell recruitment that requires Mac-1-integrin. *EMBO J.* 26, 1129-1139 (2007).
33. Zhu, S. et al. Spermine protects mice against lethal sepsis partly by attenuating surrogate inflammatory markers. *Mol. Med* 15, 275-282 (2009).
34. Andersson, U. et al. High Mobility Group 1 Protein (HMG-1) Stimulates Proinflammatory Cytokine Synthesis in Human Monocytes. *J Exp Med* 192, 565-570 (2000).
35. Yang, H. et al. Reversing established sepsis with antagonists of endogenous high-mobility group box 1. *Proc Natl Acad Sci USA* 101, 296-301 (2004).
36. Wang, H., Yang, H., Czura, C. J., Sama, A. E. & Tracey, K. J. HMGB1 as a Late Mediator of Lethal Systemic Inflammation. *Am J Respir Crit Care Med* 164, 1768-1773 (2001).
37. Qin, S. et al. Role of HMGB1 in apoptosis-mediated sepsis lethality. *J Exp. Med* 203, 1637-1642 (2006).
38. Ulloa, L. et al. Ethyl pyruvate prevents lethality in mice with established lethal sepsis and systemic inflammation. *Proc Natl Acad Sci USA* 99, 12351-12356 (2002).
39. Chen, G. et al. Suppression of HMGB1 release by stearoyl lysophosphatidylcholine: an additional mechanism for its therapeutic effects in experimental sepsis. *J. Lipid Res.* 46, 623-627 (2005).
40. Wang, H. et al. The Aqueous Extract of a Popular Herbal Nutrient Supplement, *Angelica sinensis*, Protects Mice against Lethal Endotoxemia and Sepsis. *J Nutr* 136, 360-365 (2006).
41. Li, W. et al. A Major Ingredient of Green Tea Rescues Mice from Lethal Sepsis Partly by Inhibiting HMGB1. *PLoS ONE* 2, e1153 (2007).
42. Wang, H. et al. Cholinergic agonists inhibit HMGB1 release and improve survival in experimental sepsis. *Nat. Med* 10, 1216-1221 (2004).
43. Wang, H., Czura, C. J. & Tracey, K. J. Lipid unites disparate syndromes of sepsis. *Nat. Med* 10, 124-125 (2004).
44. Pavlov, V. A. et al. Selective alpha7-nicotinic acetylcholine receptor agonist GTS-21 improves survival in murine endotoxemia and severe sepsis. *Crit Care Med.* 35, 1139-1144 (2007).
45. Parrish, W. R. et al. Modulation of TNF release by choline requires alpha7 subunit nicotinic acetylcholine receptor-mediated signaling. *Mol. Med* 14, 567-574 (2008).
46. Matthay, M. A. & Ware, L. B. Can nicotine treat sepsis? *Nat. Med* 10, 1161-1162 (2004).
47. Wheeler, D. S. et al. The green tea polyphenol epigallocatechin-3-gallate improves systemic hemodynamics and survival in rodent models of polymicrobial sepsis. *Shock* 28, 353-359 (2007).
48. O'Connor, K. A. et al. Further characterization of high mobility group box 1 (HMGB1) as a proinflammatory cytokine: central nervous system effects. *Cytokine* 24, 254-265 (2003).
49. Sappington, P. L. et al. HMGB1 B box increases the permeability of Caco-2 enterocytic monolayers and impairs intestinal barrier function in mice. *Gastroenterology* 123, 790-802 (2002).
50. Abraham, E., Arcaroli, J., Carmody, A., Wang, H. & Tracey, K. J. HMG-1 as a mediator of acute lung inflammation. *J Immunol* 165, 2950-2954 (2000).
51. Ueno, H. et al. Contributions of high mobility group box protein in experimental and clinical acute lung injury. *Am. J. Respir. Crit Care Med* 170, 1310-1316 (2004).
52. Lin, X. et al. {alpha}-Chemokine receptor blockade reduces high mobility group box 1 protein-induced lung inflammation and injury and improves survival in sepsis. *Am. Physiol Lung Cell Mol. Physiol* 289, L583-L590 (2005).
53. Rowe, S. M. et al. Potential Role of High Mobility Group Box 1 in Cystic Fibrosis Airway Disease. *Am. J. Respir. Crit Care Med* (2008).
54. Wang, H., Yang, H. & Tracey, K. J. Extracellular role of HMGB1 in inflammation and sepsis. *J Intern. Med* 255, 320-331 (2004).
55. Wang, H., Zhu, S., Zhou, R., Li, W. & Sama, A. E. Therapeutic potential of HMGB1-targeting agents in sepsis. *Expert. Rev. Mol. Med* 10, e32 (2008).
56. Wang, H., Ward, M. F. & Sama, A. E. Novel HMGB1-inhibiting therapeutic agents for experimental sepsis. *Shock.* 32, 348-357 (2009).
57. Daveau, M. et al. The synthesis of human alpha-2-HS glycoprotein is down-regulated by cytokines in hepatoma HepG2 cells. *FEBS Lett* 241, 191-194 (1988).
58. Li, W. et al. A hepatic protein, fetuin-A, occupies a protective role in lethal systemic inflammation. *PLoS ONE* 6, e16945 (2011).
59. Wang, H. et al. Peripheral administration of fetuin-A attenuates early cerebral ischemic injury in rats. *J. Cereb. Blood Flow Metab.* 30, 493-504 (2010).
60. Rosenthal, C. J., Franklin, E. C., Frangione, B. & Greenspan, J. Isolation and partial characterization of SAA—an amyloid-related protein from human serum. *J. Immunol.* 116, 1415-1418 (1976).
61. Hudgins, L. C. et al. A single intravenous dose of endotoxin rapidly alters serum lipoproteins and lipid transfer proteins in normal volunteers. *J. Lipid Res.* 44, 1489-1498 (2003).
62. Ray, B. K. & Ray, A. Involvement of an SAF-like transcription factor in the activation of serum amyloid A gene in monocyte/macrophage cells by lipopolysaccharide. Biochemistry. 36, 4662-4668 (1997).
63. Ganapathi, M. K., Rzewnicki, D., Samols, D., Jiang, S. L. & Kushner, I. Effect of combinations of cytokines and hormones on synthesis of serum amyloid A and C-reactive protein in Hep 3B cells. *J. Immunol.* 147, 1261-1265 (1991).

64. Yamada, T., Wada, A., Itoh, K. & Igari, J. Serum amyloid A secretion from monocytic leukaemia cell line THP-1 and cultured human peripheral monocytes. *Scand Immunol.* 52, 7-12 (2000).
65. Ramadori, G., Sipe, J. D., Dinarello, C. A., Mizel, S. B. & Colten, H. R. Pretranslational modulation of acute phase hepatic protein synthesis by murine recombinant interleukin 1 (IL-1) and purified human IL-1. *J. Exp. Med.* 162, 930-942 (1985).
66. Jiang, S. L., Lozanski, G., Samols, D. & Kushner, I. Induction of human serum amyloid A in Hep 3B cells by IL-6 and IL-1 beta involves both transcriptional and post-transcriptional mechanisms. *J. Immunol.* 154, 825-831 (1995).
67. Maury, C. P., Enholm, E. & Teppo, A. M. Is interferon an "inducer" of serum amyloid A? *N Engl. J. Med.* 309, 1060-1061 (1983).
68. Urieli-Shoval, S., Meek, R. L., Hanson, R. H., Eriksen, N. & Benditt, E. P. Human serum amyloid A genes are expressed in monocyte/macrophage cell lines. *Am. J. Pathol.* 145, 650-660 (1994).
69. Meek, R. L., Urieli-Shoval, S. & Benditt, E. P. Expression of apolipoprotein serum amyloid A mRNA in human atherosclerotic lesions and cultured vascular cells: implications for serum amyloid A function. *Proc. Natl. Acad. Sci. U.S.A.* 91, 3186-3190 (1994).
70. Vreugdenhil, A. C., Dentener, M. A., Snoek, A. M., Greve, J. W. & Buurman, W. A. Lipopolysaccharide binding protein and serum amyloid A secretion by human intestinal epithelial cells during the acute phase response. *J. Immunol.* 163, 2792-2798 (1999).
71. Liang, J. S. et al. Evidence for local production of acute phase response apolipoprotein serum amyloid A in Alzheimer's disease brain. *Neurosci. Lett.* 225, 73-76 (1997).
72. Ramadori, G., Sipe, J. D. & Colten, H. R. Expression and regulation of the murine serum amyloid A (SAA) gene in extrahepatic sites. *J. Immunol.* 135, 3645-3647 (1985).
73. McAdam, K. P. & Sipe, J. D. Murine model for human secondary amyloidosis: genetic variability of the acute-phase serum protein SAA response to endotoxins and casein. *Exp. Med.* 144, 1121-1127 (1976).
74. Wang, Q. et al. Endotoxemia in mice stimulates production of complement C3 and serum amyloid A in mucosa of small intestine. *Am. J Physiol.* 275, R1584-R1592 (1998).
75. O'Brien, K. D. & Chait, A. Serum amyloid A: the "other" inflammatory protein. *Curr. Atheroscler. Rep.* 8, 62-68 (2006).
76. Liuzzo, G. et al. The prognostic value of C-reactive protein and serum amyloid a protein in severe unstable angina. *N Engl. J. Med.* 331, 417-424 (1994).
77. Ryan, J., Ward, M. F. & Sama, A. E. C-reactive protein and serum amyloid A protein in unstable angina. *N Engl. J. Med.* 332, 398-399 (1995).
78. Niederau, C., Backmerhoff, F., Schumacher, B. & Niederau, C. Inflammatory mediators and acute phase proteins in patients with Crohn's disease and ulcerative colitis. *Hepatogastroenterology.* 44, 90-107 (1997).
79. Ng, P. C. et al. Host-response biomarkers for diagnosis of late-onset septicemia and necrotizing enterocolitis in preterm infants. *J. Clin. Invest.* 120, 2989-3000 (2010).
80. Cetinkaya, M., Ozkan, H., Koksal, N., Celebi, S. & Hacimustafaoglu, M. Comparison of serum amyloid A concentrations with those of C-reactive protein and procalcitonin in diagnosis and follow-up of neonatal sepsis in premature infants. *J. Perinatol.* 29, 225-231 (2009).
81. Amon, S. et al. Serum amyloid A: an early and accurate marker of neonatal early-onset sepsis. *J. Perinatol.* 27, 297-302 (2007).
82. Su, S. B. et al. A seven-transmembrane, G protein-coupled receptor, FPRL1, mediates the chemotactic activity of serum amyloid A for human phagocytic cells. *J. Exp. Med.* 189, 395-402 (1999).
83. Badolato, R. et al. Serum amyloid A is a chemoattractant: induction of migration, adhesion, and tissue infiltration of monocytes and polymorphonuclear leukocytes. *Exp. Med.* 180, 203-209 (1994).
84. Badolato, R. et al. Serum amyloid A induces calcium mobilization and chemotaxis of human monocytes by activating a pertussis toxin-sensitive signaling pathway. *J. Immunol.* 155, 4004-4010 (1995).
85. Xu, L. et al. A novel biologic function of serum amyloid A. Induction of T lymphocyte migration and adhesion. *J. Immunol.* 155, 1184-1190 (1995).
86. Olsson, N., Siegbahn, A. & Nilsson, G. Serum amyloid A induces chemotaxis of human mast cells by activating a pertussis toxin-sensitive signal transduction pathway. *Biochem. Biophys. Res. Commun.* 254, 143-146 (1999).
87. Patel, H., Fellowes, R., Coade, S. & Woo, P. Human serum amyloid A has cytokine-like properties. *Scand. J. Immunol.* 48, 410-418 (1998).
88. Song, C. et al. Serum amyloid A induction of cytokines in monocytes/macrophages and lymphocytes. *Atherosclerosis.* 207, 374-383 (2009).
89. Lachmann, H. J. et al. Natural history and outcome in systemic AA amyloidosis. *N. Engl. J. Med.* 356, 2361-2371 (2007).
90. Sandri, S. et al. Serum amyloid A induces CCL20 secretion in mononuclear cells through MAPK (p38 and ERK1/2) signaling pathways. *Immunol. Lett.* 121, 22-26 (2008).
91. Cai, H. et al. Serum amyloid A induces monocyte tissue factor. *J. Immunol.* 178, 1852-1860 (2007).
92. Furlaneto, C. J. & Campa, A. A novel function of serum amyloid A: a potent stimulus for the release of tumor necrosis factor-alpha, interleukin-1beta, and interleukin-8 by human blood neutrophil. *Biochem. Biophys. Res. Commun.* 268, 405-408 (2000).
93. Niemi, K., Baumann, M. H., Kovanen, P. T. & Eklund, K. K. Serum amyloid A (SAA) activates human mast cells which leads into degradation of SAA and generation of an amyloidogenic SAA fragment. *Biochim. Biophys. Acta.* 1762, 424-430 (2006).
94. Migita, K. et al. Serum amyloid A protein stimulates CCL20 production in rheumatoid synoviocytes. *Rheumatology.* (Oxford). 48, 741-747 (2009).
95. Sullivan, C. P., Seidl, S. E., Rich, C. B., Raymondjean, M. & Schreiber, B. M. Secretory phospholipase A2, group IIA is a novel serum amyloid A target gene: activation of smooth muscle cell expression by an interleukin-1 receptor-independent mechanism. *J. Biol. Chem.* 285, 565-575 (2010).
96. Pruzanski, W., de Beer, F. C., de Beer, M. C., Stefanski, E. & Vadas, P. Serum amyloid A protein enhances the activity of secretory non-pancreatic phospholipase A2. *Biochem. J.* 309, 461-464 (1995).

97. Shainkin-Kestenbaum, R. et al. Modulation of prostaglandin 12 production from bovine aortic endothelial cells by serum amyloid A and its N-terminal tetradecapeptide. *Biomed. Pept Proteins Nucleic Acids.* 2, 101-106 (1996).
98. Kluve-Beckerman, B., Long, G. L. & Benson, M. D. DNA sequence evidence for polymorphic forms of human serum amyloid A (SAA). *Biochem. Genet.* 24, 795-803 (1986).
99. Wang, L. & Colon, W. The interaction between apolipoprotein serum amyloid A and high-density lipoprotein. *Biochem. Biophys. Res. Commun.* 317, 157-161 (2004).
100. Ohta, S. et al. Defining lipid-binding regions of human serum amyloid A using its fragment peptides. *Chem. Phys. Lipids.* 162, 62-68 (2009).
101. Yamada, T., Kluve-Beckerman, B., Liepnieks, J. J. & Benson, M. D. In vitro degradation of serum amyloid A by cathepsin D and other acid proteases: possible protection against amyloid fibril formation. Scand. *J. Immunol.* 41, 570-574 (1995).
102. Westermark, G. T., Engstrom, U. & Westermark, P. The N-terminal segment of protein AA determines its fibrillogenic property. *Biochem. Biophys. Res. Commun.* 182, 27-33 (1992).
103. Egashira, M., Takase, H., Yamamoto, I., Tanaka, M. & Saito, H. Identification of regions responsible for heparin-induced amyloidogenesis of human serum amyloid A using its fragment peptides. *Arch. Biochem. Biophys.* 511, 101-106 (2011).
104. Preciado-Patt, L. et al. Inhibition of cell adhesion to glycoproteins of the extracellular matrix by peptides corresponding to serum amyloid A. Toward understanding the physiological role of an enigmatic protein. *Eur. J. Biochem.* 223, 35-42 (1994).
105. Urieli-Shoval, S. et al. Adhesion of human platelets to serum amyloid A. *Blood.* 99, 1224-1229 (2002).
106. Lavie, G., Zucker-Franklin, D. & Franklin, E. C. Degradation of serum amyloid A protein by surface-associated enzymes of human blood monocytes. *J. Exp. Med.* 148, 1020-1031 (1978).
107. Silverman, S. L., Cathcart, E. S., Skinner, M. & Cohen, A. S. The degradation of serum amyloid A protein by activated polymorphonuclear leucocytes: participation of granulocytic elastase. *Immunology.* 46, 737-744 (1982).
108. Lavie, G., Zucker-Franklin, D. & Franklin, E. C. Elastase-type proteases on the surface of human blood monocytes: possible role in amyloid formation. *J. Immunol.* 125, 175-180 (1980).
109. Yavin, E. J. et al. Serum amyloid A-derived peptides, present in human rheumatic synovial fluids, induce the secretion of interferon-gamma by human CD(4)(+) T-lymphocytes. *FEBS Lett.* 472, 259-262 (2000).
110. D'Amore, J. et al. The Presence and Persistence of HMGB1 Serum Levels In the Development and Progression of Clinical Sepsis. *Annals of Emergency Medicine* 56(3 (supplement)), S113-S114. 2010.
111. Osuchowski, M. F., Welch, K., Siddiqui, J. & Remick, D. G. Circulating cytokine/inhibitor profiles reshape the understanding of the SIRS/CARS continuum in sepsis and predict mortality. *J Immunol.* 177, 1967-1974 (2006).
112. Heuer, J. G. et al. Evaluation of protein C and other biomarkers as predictors of mortality in a rat cecal ligation and puncture model of sepsis. *Crit Care Med.* 32, 1570-1578 (2004).
113. Bozza, F. A. et al. Cytokine profiles as markers of disease severity in sepsis: a multiplex analysis. *Crit Care* 11, R49 (2007).
114. Clark, J. A., Clark, A. T., Hotchkiss, R. S., Buchman, T. G. & Coopersmith, C. M. Epidermal growth factor treatment decreases mortality and is associated with improved gut integrity in sepsis. *Shock.* 30, 36-42 (2008).
115. Lakota, K. et al. Could antibodies against serum amyloid A function as physiological regulators in humans? *Autoimmunity.* 44, 149-158 (2011).
116. Lakota, K. et al. Antibodies against acute phase proteins and their functions in the pathogenesis of disease: A collective profile of 25 different antibodies. *Autoimmun. Rev.* (2011).
117. Eskandari, M. K. et al. Anti-tumor necrosis factor antibody therapy fails to prevent lethality after cecal ligation and puncture or endotoxemia. *J Immunol* 148, 2724-2730 (1992).
118. Sander, L. E. et al. Hepatic acute-phase proteins control innate immune responses during infection by promoting myeloid-derived suppressor cell function. *J. Exp. Med.* 207, 1453-1464 (2010).

What is claimed is:

1. A fusion protein comprising an immunoglobulin fragment crystallizable region (Fc) and a peptide consisting of SEQ ID NO:8 or SEQ ID NO:9, wherein the fusion protein does not comprise SEQ ID NO:10, 11 or 12.

2. The fusion protein of claim 1, wherein the peptide comprises SEQ ID NO:9.

3. The fusion protein of claim 1, wherein all amino acid residues of the peptide are D-amino acids.

4. The fusion protein of claim 1, wherein all amino add residues of the peptide are L-amino acids.

5. The fusion protein of claim 1, wherein the composition comprises a carrier.

6. The fusion protein of claim 5, wherein the carrier is a pharmaceutically acceptable carrier.

7. The fusion protein of claim 1, wherein the fusion protein comprises the isolated peptide bonded via a peptide bond at an N-terminal thereof or a C-terminal thereof to a second peptide, polypeptide or protein.

8. The fusion protein of claim 1, wherein the peptide is bonded via a peptide bond at an N-terminal thereof or a C-terminal thereof to the Fc.

9. The fusion protein of claim 8, wherein the Fe has a sequence identical to a human Fc.

\* \* \* \* \*

SEQUENCE LISTING

```
<160> NUMBER OF SEQ ID NOS: 41

<210> SEQ ID NO 1
<211> LENGTH: 18
<212> TYPE: PRT
<213> ORGANISM: Homo sapiens

<400> SEQUENCE: 1

Arg Glu Ala Asn Tyr Ile Gly Ser Asp Lys Tyr Phe His Ala Arg Gly
1               5                   10                  15

Asn Tyr

<210> SEQ ID NO 2
<211> LENGTH: 18
```

```
<212> TYPE: PRT
<213> ORGANISM: Mouse

<400> SEQUENCE: 2

Lys Glu Ala Asn Trp Lys Asn Ser Asp Lys Tyr Phe His Ala Arg Gly
1               5                   10                  15

Asn Tyr

<210> SEQ ID NO 3
<211> LENGTH: 18
<212> TYPE: PRT
<213> ORGANISM: Homo sapiens

<400> SEQUENCE: 3

Arg Ser Phe Phe Ser Phe Leu Gly Glu Ala Phe Asp Gly Ala Arg Asp
1               5                   10                  15

Met Trp

<210> SEQ ID NO 4
<211> LENGTH: 18
<212> TYPE: PRT
<213> ORGANISM: Homo sapiens

<400> SEQUENCE: 4

Gly Phe Phe Ser Phe Val His Glu Ala Phe Gln Gly Ala Gly Asp Met
1               5                   10                  15

Trp Arg

<210> SEQ ID NO 5
<211> LENGTH: 6
<212> TYPE: PRT
<213> ORGANISM: Homo sapiens

<400> SEQUENCE: 5

Asn Ser Asp Lys Tyr Phe
1               5

<210> SEQ ID NO 6
<211> LENGTH: 6
<212> TYPE: PRT
<213> ORGANISM: Homo sapiens

<400> SEQUENCE: 6

Asn Trp Lys Asn Ser Asp
1               5

<210> SEQ ID NO 7
<211> LENGTH: 6
<212> TYPE: PRT
<213> ORGANISM: Homo sapiens

<400> SEQUENCE: 7

Lys Glu Ala Asn Trp Lys
1               5

<210> SEQ ID NO 8
<211> LENGTH: 6
<212> TYPE: PRT
<213> ORGANISM: Homo sapiens

<400> SEQUENCE: 8

Lys Tyr Phe His Ala Arg
1               5
```

```
<210> SEQ ID NO 9
<211> LENGTH: 6
<212> TYPE: PRT
<213> ORGANISM: Homo sapiens

<400> SEQUENCE: 9

His Ala Arg Gly Asn Tyr
1               5

<210> SEQ ID NO 10
<211> LENGTH: 6
<212> TYPE: PRT
<213> ORGANISM: Homo sapiens

<400> SEQUENCE: 10

Arg Glu Ala Asn Tyr Ile
1               5

<210> SEQ ID NO 11
<211> LENGTH: 6
<212> TYPE: PRT
<213> ORGANISM: Homo sapiens

<400> SEQUENCE: 11

Asn Tyr Ile Gly Ser Asp
1               5

<210> SEQ ID NO 12
<211> LENGTH: 6
<212> TYPE: PRT
<213> ORGANISM: Homo sapiens

<400> SEQUENCE: 12

Gly Ser Asp Lys Tyr Phe
1               5

<210> SEQ ID NO 13
<211> LENGTH: 10
<212> TYPE: PRT
<213> ORGANISM: Homo sapiens

<400> SEQUENCE: 13

Lys Asn Ser Asp Lys Tyr Phe His Ala Arg
1               5                   10

<210> SEQ ID NO 14
<211> LENGTH: 10
<212> TYPE: PRT
<213> ORGANISM: Homo sapiens

<400> SEQUENCE: 14

Asp Lys Tyr Phe His Ala Arg Gly Asn Tyr
1               5                   10

<210> SEQ ID NO 15
<211> LENGTH: 10
<212> TYPE: PRT
<213> ORGANISM: Homo sapiens

<400> SEQUENCE: 15

Ala Asn Tyr Gln Asn Ala Asp Gln Tyr Phe
1               5                   10
```

```
<210> SEQ ID NO 16
<211> LENGTH: 10
<212> TYPE: PRT
<213> ORGANISM: Homo sapiens

<400> SEQUENCE: 16

Lys Asn Pro Asn His Phe Arg Pro Glu Gly
1               5                   10

<210> SEQ ID NO 17
<211> LENGTH: 10
<212> TYPE: PRT
<213> ORGANISM: Homo sapiens

<400> SEQUENCE: 17

Phe Arg Pro Glu Gly Leu Pro Glu Lys Tyr
1               5                   10

<210> SEQ ID NO 18
<211> LENGTH: 127
<212> TYPE: PRT
<213> ORGANISM: Homo sapiens

<400> SEQUENCE: 18

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asn Ala Arg
65                  70                  75                  80

Glu Asn Ile Gln Arg Glu Asn Ile Gln Arg Phe Phe Gly Arg Gly Ala
                85                  90                  95

Glu Asp Ser Leu Ala Asp Gln Ala Ala Asn Glu Trp Gly Arg Ser Gly
            100                 105                 110

Lys Asp Pro Asn His Phe Arg Phe Ala Gly Leu Pro Glu Lys Tyr
        115                 120                 125

<210> SEQ ID NO 19
<211> LENGTH: 104
<212> TYPE: PRT
<213> ORGANISM: Homo sapiens

<400> SEQUENCE: 19

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asn Ala Arg Glu Asn
    50                  55                  60

Ile Gln Arg Leu Thr Gly Arg Gly Ala Glu Asp Ser Leu Ala Asp Gln
65                  70                  75                  80

Ala Ala Asn Lys Trp Gly Arg Ser Gly Arg Asp Pro Asn His Phe Arg
                85                  90                  95
```

Pro Ala Gly Leu Pro Glu Lys Tyr
            100

<210> SEQ ID NO 20
<211> LENGTH: 107
<212> TYPE: PRT
<213> ORGANISM: Homo sapiens

<400> SEQUENCE: 20

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asp Ala Arg Glu Asn
    50                  55                  60

Ile Gln Arg Phe Gly His Gly Ala Glu Asp Ser Leu Ala Asp Gln
65                  70                  75                  80

Ala Ala Asn Glu Trp Gly Arg Ser Gly Lys Ser Gly Lys Asp Pro Asn
                85                  90                  95

His Phe Arg Pro Ala Gly Leu Ser Glu Lys Tyr
            100                 105

<210> SEQ ID NO 21
<211> LENGTH: 104
<212> TYPE: PRT
<213> ORGANISM: Homo sapiens

<400> SEQUENCE: 21

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asn Ala Arg Glu Asn
    50                  55                  60

Ile Gln Arg Phe Gly Arg Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Ser Glu Lys Tyr
            100

<210> SEQ ID NO 22
<211> LENGTH: 103
<212> TYPE: PRT
<213> ORGANISM: Mus musculus

<400> SEQUENCE: 22

Gly Phe Phe Ser Phe Val His Glu Ala Phe Gln Gly Ala Gly Asp Met
1               5                   10                  15

Trp Arg Ala Tyr Thr Asp Met Lys Glu Ala Asn Trp Lys Asn Ser Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Gly Arg Glu Ala Phe

```
                    50                  55                  60
Gln Glu Phe Phe Gly Arg Gly His Glu Asp Thr Ile Ala Asp Gln Glu
 65                  70                  75                  80

Ala Asn Arg His Gly Arg Ser Gly Lys Asp Pro Asn Tyr Tyr Arg Pro
                 85                  90                  95

Pro Gly Leu Pro Asp Lys Tyr
            100
```

<210> SEQ ID NO 23
<211> LENGTH: 103
<212> TYPE: PRT
<213> ORGANISM: Mus musculus

<400> SEQUENCE: 23

```
Gly Phe Phe Ser Phe Ile Gly Glu Ala Phe Gln Gly Ala Gly Asp Met
  1               5                  10                  15

Trp Arg Ala Tyr Thr Asp Met Lys Glu Ala Gly Trp Lys Asp Gly Asp
                 20                  25                  30

Lys Tyr Phe His Ala Arg Gly Asn Tyr Asp Ala Ala Gln Arg Gly Pro
                 35                  40                  45

Gly Gly Val Trp Ala Ala Glu Lys Ile Ser Asp Ala Arg Glu Ser Phe
             50                  55                  60

Gln Glu Phe Phe Gly Arg Gly His Glu Asp Thr Met Ala Asp Gln Glu
 65                  70                  75                  80

Ala Asn Arg His Gly Arg Ser Gly Lys Asp Pro Asn Tyr Tyr Arg Pro
                 85                  90                  95

Pro Gly Leu Pro Ala Lys Tyr
            100
```

<210> SEQ ID NO 24
<211> LENGTH: 10
<212> TYPE: PRT
<213> ORGANISM: Mus musculus

<400> SEQUENCE: 24

```
Arg Ala Tyr Thr Asp Met Lys Glu Ala Asn
  1               5                  10
```

<210> SEQ ID NO 25
<211> LENGTH: 10
<212> TYPE: PRT
<213> ORGANISM: Mus musculus

<400> SEQUENCE: 25

```
Met Lys Glu Ala Asn Trp Lys Asn Ser Asp
  1               5                  10
```

<210> SEQ ID NO 26
<211> LENGTH: 10
<212> TYPE: PRT
<213> ORGANISM: Mus musculus

<400> SEQUENCE: 26

```
Ala Asn Trp Lys Asn Ser Asp Lys Tyr Phe
  1               5                  10
```

<210> SEQ ID NO 27
<211> LENGTH: 10
<212> TYPE: PRT
<213> ORGANISM: Mus musculus -continued

<400> SEQUENCE: 27

Lys Asn Ser Asp Lys Tyr Phe His Ala Arg
1               5                   10

<210> SEQ ID NO 28
<211> LENGTH: 10
<212> TYPE: PRT
<213> ORGANISM: Mus musculus

<400> SEQUENCE: 28

Asp Lys Tyr Phe His Ala Arg Gly Asn Tyr
1               5                   10

<210> SEQ ID NO 29
<211> LENGTH: 10
<212> TYPE: PRT
<213> ORGANISM: Homo sapiens

<400> SEQUENCE: 29

Trp Gly Arg Ser Gly Lys Asn Pro Asn His
1               5                   10

<210> SEQ ID NO 30
<211> LENGTH: 10
<212> TYPE: PRT
<213> ORGANISM: Homo sapiens

<400> SEQUENCE: 30

Phe Arg Pro Glu Gly Leu Pro Glu Lys Tyr
1               5                   10

<210> SEQ ID NO 31
<211> LENGTH: 10
<212> TYPE: PRT
<213> ORGANISM: Homo sapiens

<400> SEQUENCE: 31

Arg Ala Tyr Arg Asp Asn Leu Glu Ala Asn
1               5                   10

<210> SEQ ID NO 32
<211> LENGTH: 10
<212> TYPE: PRT
<213> ORGANISM: Homo sapiens

<400> SEQUENCE: 32

Asp Asn Leu Glu Ala Asn Tyr Gln Asn Ala
1               5                   10

<210> SEQ ID NO 33
<211> LENGTH: 10
<212> TYPE: PRT
<213> ORGANISM: Homo sapiens

<400> SEQUENCE: 33

Ala Asn Tyr Gln Asn Ala Asp Gln Tyr Phe
1               5                   10

<210> SEQ ID NO 34
<211> LENGTH: 10
<212> TYPE: PRT
<213> ORGANISM: Homo sapiens

<400> SEQUENCE: 34

Asn Ala Asp Gln Tyr Phe Tyr Ala Arg Gly
1               5                   10

<210> SEQ ID NO 35
<211> LENGTH: 10
<212> TYPE: PRT
<213> ORGANISM: Homo sapiens

<400> SEQUENCE: 35

Lys Asn Pro Asn His Phe Arg Pro Glu Gly
1               5                   10

<210> SEQ ID NO 36
<211> LENGTH: 7
<212> TYPE: PRT
<213> ORGANISM: Homo sapiens

<400> SEQUENCE: 36

Arg Glu Asn Ile Gln Arg Phe
1               5

<210> SEQ ID NO 37
<211> LENGTH: 7
<212> TYPE: PRT
<213> ORGANISM: Homo sapiens

<400> SEQUENCE: 37

Lys Tyr Phe His Ala Arg Gly
1               5

<210> SEQ ID NO 38
<211> LENGTH: 16
<212> TYPE: PRT
<213> ORGANISM: Homo sapiens

<400> SEQUENCE: 38

Arg Ser Phe Phe Ser Phe Leu Gly Glu Ala Phe Asp Gly Ala Arg Asp
1               5                   10                  15

<210> SEQ ID NO 39
<211> LENGTH: 10
<212> TYPE: PRT
<213> ORGANISM: Homo sapiens

<400> SEQUENCE: 39

Arg Glu Ala Asn Tyr Ile Gly Ser Asp Lys
1               5                   10

<210> SEQ ID NO 40
<211> LENGTH: 17
<212> TYPE: PRT
<213> ORGANISM: Homo sapiens

<400> SEQUENCE: 40

Arg Gly Pro Gly Gly Val Trp Ala Ala Glu Ala Ile Ser Asp Ala Arg
1               5                   10                  15

Glu

<210> SEQ ID NO 41
<211> LENGTH: 22
<212> TYPE: PRT
<213> ORGANISM: Homo sapiens

<400> SEQUENCE: 41

```
Arg Phe Phe Gly His Gly Ala Glu Asp Ser Leu Ala Asp Gln Ala Ala
1               5                   10                  15

Asn Glu Trp Gly Arg Ser
            20
```